US012781285B2

(12) United States Patent
Kubicek et al.

(10) Patent No.: US 12,781,285 B2
(45) Date of Patent: Nov. 3, 2026

(54) METHOD FOR POOLED INTRON TAGGING FOR REAL TIME DRUG SCREENING

(71) Applicant: CeMM—Forschungszentrum für Molekulare Medizin GmbH, Vienna (AT)

(72) Inventors: Stefan Kubicek, Vienna (AT); Andreas Reicher, Vienna (AT)

(73) Assignee: CeMM—Forschungszentrum für Molekulare Medizin GmbH, Vienna (AT)

( * ) Notice: Subject to any disclaimer, the term of this patent is extended or adjusted under 35 U.S.C. 154(b) by 868 days.

(21) Appl. No.: 17/778,927

(22) PCT Filed: Nov. 16, 2020

(86) PCT No.: PCT/EP2020/082295

§ 371 (c)(1),
(2) Date: May 23, 2022

(87) PCT Pub. No.: WO2021/099273

PCT Pub. Date: May 27, 2021

(65) Prior Publication Data

US 2024/0141445 A1 May 2, 2024

(30) Foreign Application Priority Data

Nov. 22, 2019 (EP) .................................... 19211077

(51) Int. Cl.

*C12Q 1/6897* (2018.01)
*C12N 15/10* (2006.01)
*G01N 33/50* (2006.01)

(52) U.S. Cl.

CPC ....... *C12Q 1/6897* (2013.01); *C12N 15/1086* (2013.01); *G01N 33/5038* (2013.01); *G01N 2500/10* (2013.01)

(58) Field of Classification Search

CPC .............. C12Q 1/6897; C12N 15/1086; C12N 15/1065; G01N 33/5038; G01N 2500/10
See application file for complete search history.

(56) References Cited

U.S. PATENT DOCUMENTS

| | | | |
|---|---|---|---|
| 10,240,167 | B2 | 3/2019 | Gill et al. |
| 2019/0153440 | A1 | 5/2019 | Kantardzhieva et al. |
| 2020/0299682 | A1 | 9/2020 | Prissette et al. |
| 2024/0401027 | A1 | 12/2024 | Reicher et al. |

FOREIGN PATENT DOCUMENTS

| | | |
|---|---|---|
| EP | 3031921 | 6/2016 |
| EP | 3363903 | 8/2018 |
| EP | 3417880 | 12/2018 |
| WO | WO2018170340 | 9/2018 |
| WO | WO2018195019 | 10/2018 |
| WO | WO2019210268 | 10/2019 |
| WO | WO 2020/214885 | 10/2020 |
| WO | WO 2021/099273 | 5/2021 |
| WO | WO 2023/046996 | 3/2023 |

OTHER PUBLICATIONS

Hasle et al., "High-throughput, microscope-based sorting to dissect cellular heterogeneity," Molecular Systems Biology 16(e9442):1-18, 2020.
McCarty et al., "Multiplexes CRISPR technologies for gene editing and transcriptional regulation," Nature Communication 11(1291):1-13, 2020.
Reicher et al., "Pooled protein tagging, cellular imaging, and in situ sequencing for monitoring drug action in real time," Genome Research 30:1846-1855, 2020.
Roberts et al., "Systematic gene tagging using CRISPR/Cas9 in human stem cells to illuminate cell organization," Molecular Biology of the Cell 28:2854-2874, 2017.
Thöne et al., "CRISPR/Cas9-mediated generic protein tagging in mammalian cells," Method 164-165:59-66, 2019.
Xiang et al., "Enhancing CRISPR-Cas9 gRNA efficiency prediction by data integration and deep learning," Nature Communications 12(3238):1-9, 2021.
Zhong et al., "High-fidelity, efficient, and reversible labeling of endogenous proteins using CRISPR-based designer exon insertion," eLife 10(e64911):1-21, 2021.
Chen et al., "Efficient labeling an dimaging of protein-coding genes in living cells using CRISPR-Tag", *Nature Communications*, 9:5065, 2018.
Giuliano et al., "Generating single cell-derived knockout clones in mammalian cells with CRISPR/Cas 9", *PeerJPreprints*, Jan. 31, 2019.
International Preliminary Report on Patentability for PCT/EP2020/082295 dated May 17, 2022, 7 pages.
International Search Report and Written Opinion for PCT/EP2020/082295 dated Jan. 22, 2021, 13 pages.
Serebrenik et al., "Efficient and flexible tagging of endogenous genes by homology-independent intron targeting", *Genome Research*, 29:1322-1328, 2019.

*Primary Examiner* — Iqbal H Chowdhury
(74) *Attorney, Agent, or Firm* — pH IP Law

(57) ABSTRACT

The present invention relates to a method for monitoring the effect of an environmental factor on the proteome of a cell. Furthermore, cell populations are provided that comprise multiple cells each comprising an inserted tag sequence in an intron of said cell, wherein the tag is inserted in-frame with the preceding exonic sequence and wherein the intron into which the tag is inserted is different between cells.

20 Claims, 20 Drawing Sheets

Figure 1:
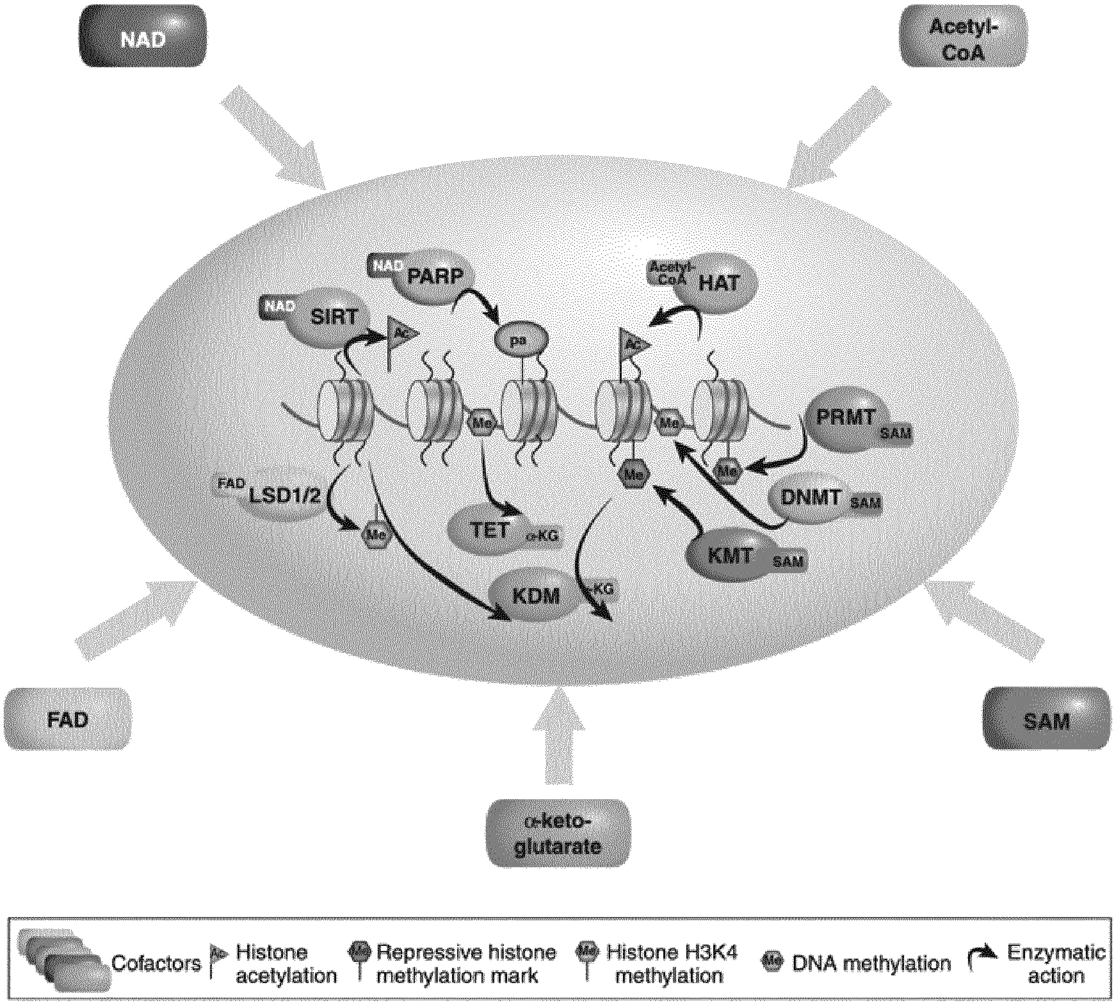

Specification includes a Sequence Listing.

b

2,889 target genes sgRNA library
14,146 sgRNAs
11,614 introns
2,390 genes c d

GFP-tagged cell pool
1,777 sgRNAs
1,650 introns
953 genes e f a b a b

Figure 5 cont.

c

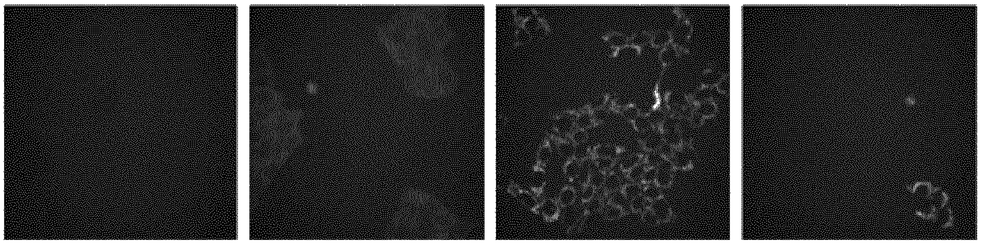

ABAT, Intron 12_1
Mitochondria (weak)
Human Protein Atlas:
Mitochondria
M_id

ACAA1, Intron 1_2
Cytoplasm, Nucleus
Human Protein Atlas:
Peroxisomes
C_dis

ACAT1, Intron 1_1
Mitochondria
Human Protein Atlas:
Mitochondria
M_id

ACAT1, Intron 5_1
Mitochondria
Human Protein Atlas:
Mitochondria
M_id

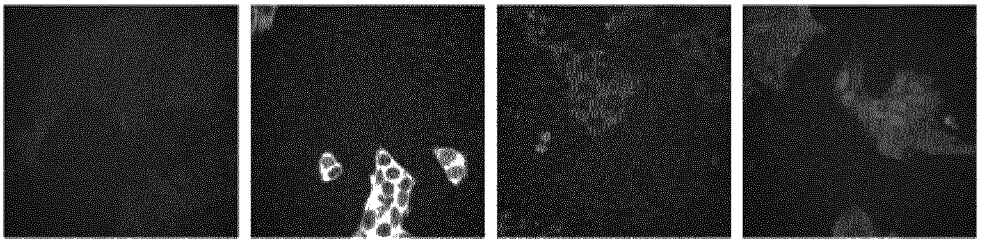

ACBD7, Intron 1_3
Cytoplasm, Nucleus
Human Protein Atlas:
Vesicles, Cytosol
C_sim ACLY, Intron 7_1
Cytoplasm, Nucleus
Human Protein Atlas: Plasma
membrane, Cytosol,
Nucleoplasm; C_id ACLY, Intron 10_1
Cytoplasm, Nucleus
Human Protein Atlas: Plasma
membrane, Cytosol,
Nucleoplasm, C_id ACLY, Intron 22_1
Cytoplasm, Nucleus
Human Protein Atlas: Plasma
membrane, Cytosol,
Nucleoplasm, C_id

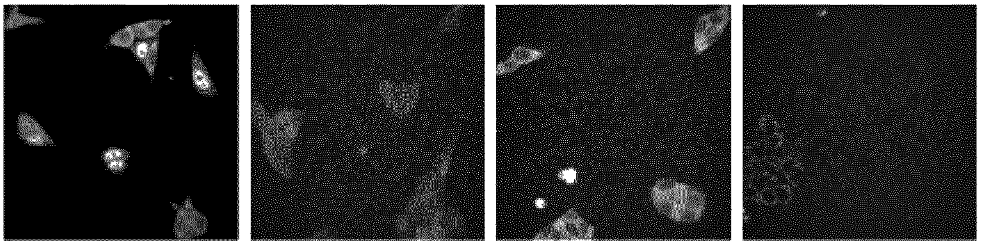

ACLY, Intron 22_1
Cytoplasm, Nucleus
Human Protein Atlas: Plasma
membrane, Cytosol,
Nucleoplasm, C_id ACLY, Intron 22_1
Cytoplasm, Nucleus
Human Protein Atlas: Plasma
membrane, Cytosol,
Nucleoplasm, C_id ACLY, Intron 24_1
Cytoplasm, Nucleus
Human Protein Atlas: Plasma
membrane, Cytosol,
Nucleoplasm, C_id ACO2, Intron 8_1
Mitochondria
Human Protein Atlas:
Mitochondria
M_id

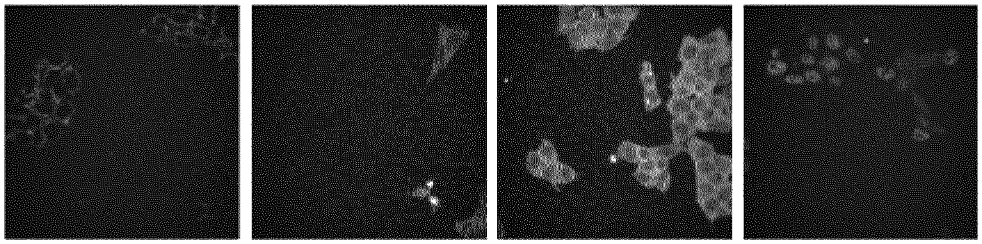

ACO2, Intron 15_1
Mitochondria
Human Protein Atlas:
Mitochondria
M_id

ACOT7, Intron 2_2
Cytoplasm, Nucleus
Human Protein Atlas: Cytosol,
Nucleoplasm
C_id ACOT7, Intron 2_2
Cytoplasm, Nucleus
Human Protein Atlas: Cytosol,
Nucleoplasm
C_id AKAP8L, Intron 13_1
Nucleus
Human Protein Atlas: Nuclear
speckles
N_id d a

SEQUENCE LISTING

<160> NUMBER OF SEQ ID NOS: 67

<210> SEQ ID NO 1
<211> LENGTH: 24
<212> TYPE: RNA
<213> ORGANISM: Artificial Sequence
<220> FEATURE:
<223> OTHER INFORMATION: Primer CROP-seq sgRNA amplicon fwd

<400> SEQUENCE: 1
atcttgtgga aaggacgaaa cacc 24

<210> SEQ ID NO 2
<211> LENGTH: 23
<212> TYPE: RNA
<213> ORGANISM: Artificial Sequence
<220> FEATURE:
<223> OTHER INFORMATION: Primer CROP-seq sgRNA amplicon rev

<400> SEQUENCE: 2
tgtctcaaga tctagttacg cca 23

<210> SEQ ID NO 3
<211> LENGTH: 25
<212> TYPE: DNA
<213> ORGANISM: Artificial Sequence
<220> FEATURE:
<223> OTHER INFORMATION: Primer oRT_CROPseq

<400> SEQUENCE: 3
gactagcctt attttaactt gctat 25

<210> SEQ ID NO 4
<211> LENGTH: 77
<212> TYPE: DNA
<213> ORGANISM: Artificial Sequence
<220> FEATURE:
<223> OTHER INFORMATION: Primer oPD_CROPseq
<220> FEATURE:
<221> NAME/KEY: modified_base
<222> LOCATION: 1
<223> OTHER INFORMATION: /mod_base="OTHER"
/note="phosphorylation"

<400> SEQUENCE: 4
gttttagagc tagaaatagc aagctcctgt tcgacaccta cccacctcat cccactcttc 60
aaaaggacga aacaccg 77

<210> SEQ ID NO 5
<211> LENGTH: 35
<212> TYPE: DNA
<213> ORGANISM: Artificial Sequence
<220> FEATURE:
<223> OTHER INFORMATION: Primer oSBS_CROPseq

<400> SEQUENCE: 5
cacctcatcc cactcttcaa aaggacgaaa caccg 35

<210> SEQ ID NO 6
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_1

<400> SEQUENCE: 6
gagaaatctt gtggaaagga cgaaacac 28

<210> SEQ ID NO 7
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_2

<400> SEQUENCE: 7
caagaatctt gtggaaagga cgaaacac 28

<210> SEQ ID NO 8
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_3

<400> SEQUENCE: 8
gaacaatctt gtggaaagga cgaaacac 28

<210> SEQ ID NO 9
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_4

<400> SEQUENCE: 9
ccataatctt gtggaaagga cgaaacac 28

<210> SEQ ID NO 10
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_5

<400> SEQUENCE: 10
gttagatctt gtggaaagga cgaaacac 28

<210> SEQ ID NO 11
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_6

<400> SEQUENCE: 11
actcgatctt gtggaaagga cgaaacac 28

<210> SEQ ID NO 12
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_7

<400> SEQUENCE: 12
tgttgatctt gtggaaagga cgaaacac 28

<210> SEQ ID NO 13
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_8

<400> SEQUENCE: 13
aggtcatctt gtggaaagga cgaaacac 28

<210> SEQ ID NO 14
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_9

<400> SEQUENCE: 14
aggaaatctt gtggaaagga cgaaacac 28

<210> SEQ ID NO 15
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_10

<400> SEQUENCE: 15
acagaatctt gtggaaagga cgaaacac 28

<210> SEQ ID NO 16
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_11

<400> SEQUENCE: 16
agacaatctt gtggaaagga cgaaacac 28

<210> SEQ ID NO 17
<211> LENGTH: 28
<212> TYPE: DNA
<213> ORGANISM: Artificial Sequence
<220> FEATURE:
<223> OTHER INFORMATION: multiplexed amplicon sequencing barcodes FWD1_12

<400> SEQUENCE: 17
tggtaatctt gtggaaagga cgaaacac 28

<210> SEQ ID NO 18
<211> LENGTH: 28
<212> TYPE: DNA
<213> ORGANISM: Artificial Sequence
<220> FEATURE:
<223> OTHER INFORMATION: multiplexed amplicon sequencing barcodes FWD2_1

<400> SEQUENCE: 18
ctaggatctt gtggaaagga cgaaacac 28

<210> SEQ ID NO 19
<211> LENGTH: 28
<212> TYPE: DNA
<213> ORGANISM: Artificial Sequence
<220> FEATURE:
<223> OTHER INFORMATION: multiplexed amplicon sequencing barcodes FWD2_2

<400> SEQUENCE: 19
cgatgatctt gtggaaagga cgaaacac 28

<210> SEQ ID NO 20
<211> LENGTH: 28
<212> TYPE: DNA
<213> ORGANISM: Artificial Sequence
<220> FEATURE:
<223> OTHER INFORMATION: multiplexed amplicon sequencing barcodes FWD2_3

<400> SEQUENCE: 20
ttcgcatctt gtggaaagga cgaaacac 28

<210> SEQ ID NO 21
<211> LENGTH: 28
<212> TYPE: DNA
<213> ORGANISM: Artificial Sequence
<220> FEATURE:
<223> OTHER INFORMATION: multiplexed amplicon sequencing barcodes FWD2_4

<400> SEQUENCE: 21
ggttcatctt gtggaaagga cgaaacac 28

<210> SEQ ID NO 22
<211> LENGTH: 28
<212> TYPE: DNA
<213> ORGANISM: Artificial Sequence
<220> FEATURE:
<223> OTHER INFORMATION: multiplexed amplicon sequencing barcodes FWD2_5

<400> SEQUENCE: 22
ccgaaatctt gtggaaagga cgaaacac 28

<210> SEQ ID NO 23
<211> LENGTH: 28
<212> TYPE: DNA
<213> ORGANISM: Artificial Sequence
<220> FEATURE:
<223> OTHER INFORMATION: multiplexed amplicon sequencing barcodes FWD2_6

<400> SEQUENCE: 23
tcggaatctt gtggaaagga cgaaacac 28

<210> SEQ ID NO 24
<211> LENGTH: 28
<212> TYPE: DNA
<213> ORGANISM: Artificial Sequence
<220> FEATURE:
<223> OTHER INFORMATION: multiplexed amplicon sequencing barcodes FWD2_7

<400> SEQUENCE: 24
aagcaatctt gtggaaagga cgaaacac 28

<210> SEQ ID NO 25
<211> LENGTH: 28
<212> TYPE: DNA
<213> ORGANISM: Artificial Sequence
<220> FEATURE:
<223> OTHER INFORMATION: multiplexed amplicon sequencing barcodes FWD2_8

<400> SEQUENCE: 25
tcctaatctt gtggaaagga cgaaacac 28

<210> SEQ ID NO 26
<211> LENGTH: 28
<212> TYPE: DNA

<213> ORGANISM: Artificial Sequence
<220> FEATURE:
<223> OTHER INFORMATION: multiplexed amplicon sequencing barcodes FWD2_9

<400> SEQUENCE: 26
aatggatctt gtggaaagga cgaaacac 28

<210> SEQ ID NO 27
<211> LENGTH: 28
<212> TYPE: DNA
<213> ORGANISM: Artificial Sequence
<220> FEATURE:
<223> OTHER INFORMATION: multiplexed amplicon sequencing barcodes
FWD2_10

<400> SEQUENCE: 27
gcatgatctt gtggaaagga cgaaacac 28

<210> SEQ ID NO 28
<211> LENGTH: 28
<212> TYPE: DNA
<213> ORGANISM: Artificial Sequence
<220> FEATURE:
<223> OTHER INFORMATION: multiplexed amplicon sequencing barcodes
FWD2_11

<400> SEQUENCE: 28
tatgcatctt gtggaaagga cgaaacac 28

<210> SEQ ID NO 29
<211> LENGTH: 28
<212> TYPE: DNA
<213> ORGANISM: Artificial Sequence
<220> FEATURE:
<223> OTHER INFORMATION: multiplexed amplicon sequencing barcodes
FWD2_12

<400> SEQUENCE: 29
cctgtatctt gtggaaagga cgaaacac 28

<210> SEQ ID NO 30
<211> LENGTH: 28
<212> TYPE: DNA
<213> ORGANISM: Artificial Sequence
<220> FEATURE:
<223> OTHER INFORMATION: multiplexed amplicon sequencing barcodes FWD3_1

<400> SEQUENCE: 30
gtggaatctt gtggaaagga cgaaacac 28

<210> SEQ ID NO 31
<211> LENGTH: 28
<212> TYPE: DNA
<213> ORGANISM: Artificial Sequence
<220> FEATURE:
<223> OTHER INFORMATION: multiplexed amplicon sequencing barcodes FWD3_2

<400> SEQUENCE: 31
ctgcaatctt gtggaaagga cgaaacac 28

<210> SEQ ID NO 32
<211> LENGTH: 28
<212> TYPE: DNA
<213> ORGANISM: Artificial Sequence
<220> FEATURE:
<223> OTHER INFORMATION: multiplexed amplicon sequencing barcodes FWD3_3

<400> SEQUENCE: 32
accaaatctt gtggaaagga cgaaacac 28

<210> SEQ ID NO 33
<211> LENGTH: 28
<212> TYPE: DNA
<213> ORGANISM: Artificial Sequence
<220> FEATURE:
<223> OTHER INFORMATION: multiplexed amplicon sequencing barcodes FWD3_4

<400> SEQUENCE: 33
tgcgaatctt gtggaaagga cgaaacac 28

<210> SEQ ID NO 34
<211> LENGTH: 28
<212> TYPE: DNA
<213> ORGANISM: Artificial Sequence
<220> FEATURE:
<223> OTHER INFORMATION: multiplexed amplicon sequencing barcodes FWD3_5

<400> SEQUENCE: 34
tgtcaatctt gtggaaagga cgaaacac 28

<210> SEQ ID NO 35
<211> LENGTH: 28
<212> TYPE: DNA
<213> ORGANISM: Artificial Sequence
<220> FEATURE:
<223> OTHER INFORMATION: multiplexed amplicon sequencing barcodes FWD3_6

<400> SEQUENCE: 35
tagagatctt gtggaaagga cgaaacac 28

<210> SEQ ID NO 36
<211> LENGTH: 28
<212> TYPE: DNA
<213> ORGANISM: Artificial Sequence
<220> FEATURE:
<223> OTHER INFORMATION: multiplexed amplicon sequencing barcodes FWD3_7

<400> SEQUENCE: 36
taccgatctt gtggaaagga cgaaacac 28

<210> SEQ ID NO 37
<211> LENGTH: 28
<212> TYPE: DNA
<213> ORGANISM: Artificial Sequence
<220> FEATURE:
<223> OTHER INFORMATION: multiplexed amplicon sequencing barcodes FWD3_8

<400> SEQUENCE: 37
ttgtgatctt gtggaaagga cgaaacac 28

<210> SEQ ID NO 38
<211> LENGTH: 28
<212> TYPE: DNA
<213> ORGANISM: Artificial Sequence
<220> FEATURE:
<223> OTHER INFORMATION: multiplexed amplicon sequencing barcodes FWD3_9

<400> SEQUENCE: 38
acaccatctt gtggaaagga cgaaacac 28

<210> SEQ ID NO 39
<211> LENGTH: 28

<212> TYPE: DNA
<213> ORGANISM: Artificial Sequence
<220> FEATURE:
<223> OTHER INFORMATION: multiplexed amplicon sequencing barcodes FWD3_10

<400> SEQUENCE: 39
accttatctt gtggaaagga cgaaacac 28

<210> SEQ ID NO 40
<211> LENGTH: 28
<212> TYPE: DNA
<213> ORGANISM: Artificial Sequence
<220> FEATURE:
<223> OTHER INFORMATION: multiplexed amplicon sequencing barcodes FWD3_11

<400> SEQUENCE: 40
ctctaatctt gtggaaagga cgaaacac 28

<210> SEQ ID NO 41
<211> LENGTH: 28
<212> TYPE: DNA
<213> ORGANISM: Artificial Sequence
<220> FEATURE:
<223> OTHER INFORMATION: multiplexed amplicon sequencing barcodes FWD3_12

<400> SEQUENCE: 41
tcacgatctt gtggaaagga cgaaacac 28

<210> SEQ ID NO 42
<211> LENGTH: 28
<212> TYPE: DNA
<213> ORGANISM: Artificial Sequence
<220> FEATURE:
<223> OTHER INFORMATION: multiplexed amplicon sequencing barcodes REV1_A

<400> SEQUENCE: 42
ggcaatgtct caagatctag ttacgcca 28

<210> SEQ ID NO 43
<211> LENGTH: 28
<212> TYPE: DNA
<213> ORGANISM: Artificial Sequence
<220> FEATURE:
<223> OTHER INFORMATION: multiplexed amplicon sequencing barcodes REV1_B

<400> SEQUENCE: 43
aacgatgtct caagatctag ttacgcca 28

<210> SEQ ID NO 44
<211> LENGTH: 28
<212> TYPE: DNA
<213> ORGANISM: Artificial Sequence
<220> FEATURE:
<223> OTHER INFORMATION: multiplexed amplicon sequencing barcodes REV1_C

<400> SEQUENCE: 44
gtccatgtct caagatctag ttacgcca 28

<210> SEQ ID NO 45
<211> LENGTH: 28
<212> TYPE: DNA
<213> ORGANISM: Artificial Sequence
<220> FEATURE:
<223> OTHER INFORMATION: multiplexed amplicon sequencing barcodes REV1_D

<400> SEQUENCE: 45
tgaagtgtct caagatctag ttacgcca 28

<210> SEQ ID NO 46
<211> LENGTH: 28
<212> TYPE: DNA
<213> ORGANISM: Artificial Sequence
<220> FEATURE:
<223> OTHER INFORMATION: multiplexed amplicon sequencing barcodes REV1_E

<400> SEQUENCE: 46
gtacgtgtct caagatctag ttacgcca 28

<210> SEQ ID NO 47
<211> LENGTH: 28
<212> TYPE: DNA
<213> ORGANISM: Artificial Sequence
<220> FEATURE:
<223> OTHER INFORMATION: multiplexed amplicon sequencing barcodes REV1_F

<400> SEQUENCE: 47
acgtgtgtct caagatctag ttacgcca 28

<210> SEQ ID NO 48
<211> LENGTH: 28
<212> TYPE: DNA
<213> ORGANISM: Artificial Sequence
<220> FEATURE:
<223> OTHER INFORMATION: multiplexed amplicon sequencing barcodes REV1_G

<400> SEQUENCE: 48
caacctgtct caagatctag ttacgcca 28

<210> SEQ ID NO 49
<211> LENGTH: 28
<212> TYPE: DNA
<213> ORGANISM: Artificial Sequence
<220> FEATURE:
<223> OTHER INFORMATION: multiplexed amplicon sequencing barcodes REV1_H

<400> SEQUENCE: 49
cactttgtct caagatctag ttacgcca 28

<210> SEQ ID NO 50
<211> LENGTH: 28
<212> TYPE: DNA
<213> ORGANISM: Artificial Sequence
<220> FEATURE:
<223> OTHER INFORMATION: multiplexed amplicon sequencing barcodes REV2_A

<400> SEQUENCE: 50
cgtaatgtct caagatctag ttacgcca 28

<210> SEQ ID NO 51
<211> LENGTH: 28
<212> TYPE: DNA
<213> ORGANISM: Artificial Sequence
<220> FEATURE:
<223> OTHER INFORMATION: multiplexed amplicon sequencing barcodes REV2_B

<400> SEQUENCE: 51
ggtgatgtct caagatctag ttacgcca 28

<210> SEQ ID NO 52

<211> LENGTH: 28
<212> TYPE: DNA
<213> ORGANISM: Artificial Sequence
<220> FEATURE:
<223> OTHER INFORMATION: multiplexed amplicon sequencing barcodes REV2_C

<400> SEQUENCE: 52
cctcatgtct caagatctag ttacgcca 28

<210> SEQ ID NO 53
<211> LENGTH: 28
<212> TYPE: DNA
<213> ORGANISM: Artificial Sequence
<220> FEATURE:
<223> OTHER INFORMATION: multiplexed amplicon sequencing barcodes REV2_D

<400> SEQUENCE: 53
atgagtgtct caagatctag ttacgcca 28

<210> SEQ ID NO 54
<211> LENGTH: 28
<212> TYPE: DNA
<213> ORGANISM: Artificial Sequence
<220> FEATURE:
<223> OTHER INFORMATION: multiplexed amplicon sequencing barcodes REV2_E

<400> SEQUENCE: 54
atccgtgtct caagatctag ttacgcca 28

<210> SEQ ID NO 55
<211> LENGTH: 28
<212> TYPE: DNA
<213> ORGANISM: Artificial Sequence
<220> FEATURE:
<223> OTHER INFORMATION: multiplexed amplicon sequencing barcodes REV2_F

<400> SEQUENCE: 55
gactgtgtct caagatctag ttacgcca 28

<210> SEQ ID NO 56
<211> LENGTH: 28
<212> TYPE: DNA
<213> ORGANISM: Artificial Sequence
<220> FEATURE:
<223> OTHER INFORMATION: multiplexed amplicon sequencing barcodes REV2_G

<400> SEQUENCE: 56
tctcctgtct caagatctag ttacgcca 28

<210> SEQ ID NO 57
<211> LENGTH: 28
<212> TYPE: DNA
<213> ORGANISM: Artificial Sequence
<220> FEATURE:
<223> OTHER INFORMATION: multiplexed amplicon sequencing barcodes REV2_H

<400> SEQUENCE: 57
gctaatgtct caagatctag ttacgcca 28

<210> SEQ ID NO 58
<211> LENGTH: 28
<212> TYPE: DNA
<213> ORGANISM: Artificial Sequence
<220> FEATURE:
<223> OTHER INFORMATION: multiplexed amplicon sequencing barcodes REV3_A

<400> SEQUENCE: 58
cttgatgtct caagatctag ttacgcca 28

<210> SEQ ID NO 59
<211> LENGTH: 28
<212> TYPE: DNA
<213> ORGANISM: Artificial Sequence
<220> FEATURE:
<223> OTHER INFORMATION: multiplexed amplicon sequencing barcodes REV3_B

<400> SEQUENCE: 59
ggatatgtct caagatctag ttacgcca 28

<210> SEQ ID NO 60
<211> LENGTH: 28
<212> TYPE: DNA
<213> ORGANISM: Artificial Sequence
<220> FEATURE:
<223> OTHER INFORMATION: multiplexed amplicon sequencing barcodes REV3_C

<400> SEQUENCE: 60
agtagtgtct caagatctag ttacgcca 28

<210> SEQ ID NO 61
<211> LENGTH: 28
<212> TYPE: DNA
<213> ORGANISM: Artificial Sequence
<220> FEATURE:
<223> OTHER INFORMATION: multiplexed amplicon sequencing barcodes REV3_D

<400> SEQUENCE: 61
gatcgtgtct caagatctag ttacgcca 28

<210> SEQ ID NO 62
<211> LENGTH: 28
<212> TYPE: DNA
<213> ORGANISM: Artificial Sequence
<220> FEATURE:
<223> OTHER INFORMATION: multiplexed amplicon sequencing barcodes REV3_E

<400> SEQUENCE: 62
agctgtgtct caagatctag ttacgcca 28

<210> SEQ ID NO 63
<211> LENGTH: 28
<212> TYPE: DNA
<213> ORGANISM: Artificial Sequence
<220> FEATURE:
<223> OTHER INFORMATION: multiplexed amplicon sequencing barcodes REV3_F

<400> SEQUENCE: 63
cttcctgtct caagatctag ttacgcca 28

<210> SEQ ID NO 64
<211> LENGTH: 28
<212> TYPE: DNA
<213> ORGANISM: Artificial Sequence
<220> FEATURE:
<223> OTHER INFORMATION: multiplexed amplicon sequencing barcodes REV3_G

<400> SEQUENCE: 64
attgctgtct caagatctag ttacgcca 28

<210> SEQ ID NO 65
<211> LENGTH: 28
<212> TYPE: DNA

<213> ORGANISM: Artificial Sequence
<220> FEATURE:
<223> OTHER INFORMATION: multiplexed amplicon sequencing barcodes REV3_H

<400> SEQUENCE: 65
gtgcttgtct caagatctag ttacgcca 28

<210> SEQ ID NO 66
<211> LENGTH: 1116
<212> TYPE: DNA
<213> ORGANISM: Artificial Sequence
<220> FEATURE:
<223> OTHER INFORMATION: GFP generic donor plasmid (relevant part)

<400> SEQUENCE: 66
atgttctttc ctgcgttatc ccctggagat cgagtgccgc atcaccggct attggtctta 60
ctgacatcca ctttgccttt ctctccacag ggtggcggtg gctcgggcgg tggtgggtcc 120
ggtggcggcg gatctggcgg tggtggatcc gtgagcaagg gcgaggagct gttcaccggg 180
gtggtgccca tcctggtcga gctggacggc gacgtaaacg gccacaagtt cagcgtgtcc 240
ggcgagggcg agggcgatgc cacctacggc aagctgaccc tgaagttcat ctgcaccacc 300
ggcaagctgc ccgtgccctg gcccaccctc gtgaccaccc tgacctacgg cgtgcagtgc 360
ttcagccgct accccgacca catgaagcag cacgacttct tcaagtccgc catgcccgaa 420
ggctacgtcc aggagcgcac catcttcttc aaggacgacg gcaactacaa gacccgcgcc 480
gaggtgaagt tcgagggcga caccctggtg aaccgcatcg agctgaaggg catcgacttc 540
aaggaggacg gcaacatcct ggggcacaag ctggagtaca actacaacag ccacaacgtc 600
tatatcatgg ccgacaagca gaagaacggc atcaaggtga acttcaagat ccgccacaac 660
atcgaggacg gcagcgtgca gctcgccgac cactaccagc agaacacccc catcggcgac 720
ggccccgtgc tgctgcccga caaccactac ctgagcaccc agtccgccct gagcaaagac 780
cccaacgaga agcgcgatca catggtcctg ctggagttcg tgaccgccgc cgggatcact 840
ctcggcatgg acgagctgta caagggcggc ggtggatccg gtggcggcgg atctggcggt 900
ggaggttcgg gtggcggtgg gtcgggcaag gtaagtatca attagaagac gaattcccgg 960
tgatgcggca ctcgatctcg aattcttaca gacaagctgt gaccgtctcc gggagctgca 1020
tgtgtcagag gttttcaccg tcatcaccga aacgcgcgag acgaaagggc ctcgtgatac 1080
gcctattttt ataggttaat gtcatgataa taatgg 1116

<210> SEQ ID NO 67
<211> LENGTH: 5071
<212> TYPE: DNA
<213> ORGANISM: Artificial Sequence
<220> FEATURE:
<223> OTHER INFORMATION: GFP minicircle

<400> SEQUENCE: 67
acattaccct gttatcccta gatacattac cctgttatcc cagatgacat accctgttat 60
ccctagatga cattaccctg ttatcccaga tgacattacc ctgttatccc tagatacatt 120
accctgttat cccagatgac ataccctgtt atccctagat gacattaccc tgttatccca 180
gatgacatta ccctgttatc cctagataca ttaccctgtt atcccagatg acataccctg 240
ttatccctag atgacattac cctgttatcc cagatgacat taccctgtta tccctagata 300
cattaccctg ttatcccaga tgacataccc tgttatccct agatgacatt accctgttat 360
cccagatgac attaccctgt tatccctaga tacattaccc tgttatccca gatgacatac 420

```
cctgttatcc ctagatgaca ttaccctgtt atcccagatg acattaccct gttatcccta    480
gatacattac cctgttatcc cagatgacat accctgttat ccctagatga cattaccctg    540
ttatcccaga tgacattacc ctgttatccc tagatacatt accctgttat cccagatgac    600
ataccctgtt atccctagat gacattaccc tgttatccca gatgacatta ccctgttatc    660
cctagataca ttaccctgtt atcccagatg acataccctg ttatccctag atgacattac    720
cctgttatcc cagataaact caatgatgat gatgatgatg gtcgagactc agcggccgcg    780
gtgccagggc gtgcccttgg gctccccggg cgcgactagt gaattcagat ctgatcctgc    840
gttatcccct ggagatcgag tgccgcatca ccggctattg gtcttactga catccacttt    900
gcctttctct ccacagggtg gcggtggctc gggcggtggt gggtccggtg gcggcggatc    960
tggcggtggt ggatccgtga gcaagggcga ggagctgttc accggggtgg tgcccatcct   1020
ggtcgagctg gacggcgacg taaacggcca caagttcagc gtgtccggcg agggcgaggg   1080
cgatgccacc tacggcaagc tgaccctgaa gttcatctgc accaccggca agctgcccgt   1140
gccctggccc accctcgtga ccaccctgac ctacggcgtg cagtgcttca gccgctaccc   1200
cgaccacatg aagcagcacg acttcttcaa gtccgccatg cccgaaggct acgtccagga   1260
gcgcaccatc ttcttcaagg acgacggcaa ctacaagacc cgcgccgagg tgaagttcga   1320
gggcgacacc ctggtgaacc gcatcgagct gaagggcatc gacttcaagg aggacggcaa   1380
catcctgggg cacaagctgg agtacaacta caacagccac aacgtctata tcatggccga   1440
caagcagaag aacggcatca aggtgaactt caagatccgc cacaacatcg aggacggcag   1500
cgtgcagctc gccgaccact accagcagaa cacccccatc ggcgacggcc ccgtgctgct   1560
gcccgacaac cactacctga gcacccagtc cgccctgagc aaagacccca acgagaagcg   1620
cgatcacatg gtcctgctgg agttcgtgac cgccgccggg atcactctcg gcatggacga   1680
gctgtacaag ggcggcggtg gatccggtgg cggcggatct ggcggtggag gttcgggtgg   1740
cggtgggtcg ggcaaggtaa gtatcaatta gaagacgaat tccatctcta gagtcgaccc   1800
atgggggccc gccccaactg gggtaacctt tgagttctct cagttggggg taatcagcat   1860
catgatgtgg taccacatca tgatgctgat tataagaatg cggccgccac actctagtgg   1920
atctcgagtt aataattcag aagaactcgt caagaaggcg atagaaggcg atgcgctgcg   1980
aatcgggagc ggcgataccg taaagcacga ggaagcggtc agcccattcg ccgccaagct   2040
cttcagcaat atcacgggta gccaacgcta tgtcctgata gcggtccgcc acacccagcc   2100
ggccacagtc gatgaatcca gaaaagcggc cattttccac catgatattc ggcaagcagg   2160
catcgccatg ggtcacgacg agatcctcgc cgtcgggcat gctcgccttg agcctggcga   2220
acagttcggc tggcgcgagc ccctgatgct cttcgtccag atcatcctga tcgacaagac   2280
cggcttccat ccgagtacgt gctcgctcga tgcgatgttt cgcttggtgg tcgaatgggc   2340
aggtagccgg atcaagcgta tgcagccgcc gcattgcatc agccatgatg gatactttct   2400
cggcaggagc aaggtgagat gacaggagat cctgccccgg cacttcgccc aatagcagcc   2460
agtcccttcc cgcttcagtg acaacgtcga gcacagctgc gcaaggaacg cccgtcgtgg   2520
ccagccacga tagccgcgct gcctcgtctt gcagttcatt cagggcaccg gacaggtcgg   2580
tcttgacaaa aagaaccggg cgcccctgcg ctgacagccg gaacacggcg gcatcagagc   2640
agccgattgt ctgttgtgcc cagtcatagc cgaatagcct ctccacccaa gcggccggag   2700
aacctgcgtg caatccatct tgttcaatca tgcgaaacga tcctcatcct gtctcttgat   2760
```

-continued

```
cagagcttga tcccctgcgc catcagatcc ttggcggcga gaaagccatc cagtttactt   2820
tgcagggctt cccaacctta ccagagggcg ccccagctgg caattccggt tcgcttgctg   2880
tccataaaac cgcccagtct agctatcgcc atgtaagccc actgcaagct acctgctttc   2940
tctttgcgct tgcgttttcc cttgtccaga tagcccagta gctgacattc atccggggtc   3000
agcaccgttt ctgcggactg gctttctacg tgctcgaggg ggccaaacg gtctccagct    3060
tggctgtttt ggcggatgag agaagatttt cagcctgata cagattaaat cagaacgcag   3120
aagcggtctg ataaaacaga atttgcctgg cggcagtagc gcggtggtcc cacctgaccc   3180
catgccgaac tcagaagtga aacgccgtag cgccgatggt agtgtggggt ctccccatgc   3240
gagagtaggg aactgccagg catcaaataa aacgaaaggc tcagtcgaaa gactgggcct   3300
ttcgttttat ctgttgtttg tcggtgaacg ctctcctgag taggacaaat ccgccgggag   3360
cggatttgaa cgttgcgaag caacggcccg gagggtggcg ggcaggacgc ccgccataaa   3420
ctgccaggca tcaaattaag cagaaggcca tcctgacgga tggccttttt gcgtttctac   3480
aaactctttt gtttattttt ctaaatacat tcaaatatgt atccgctcat gaccaaaatc   3540
ccttaacgtg agttttcgtt ccactgagcg tcagaccccg tagaaaagat caaaggatct   3600
tcttgagatc cttttttttct gcgcgtaatc tgctgcttgc aaacaaaaaa accaccgcta  3660
ccagcggtgg tttgtttgcc ggatcaagag ctaccaactc tttttccgaa ggtaactggc   3720
ttcagcagag cgcagatacc aaatactgtc cttctagtgt agccgtagtt aggccaccac   3780
ttcaagaact ctgtagcacc gcctacatac ctcgctctgc taatcctgtt accagtggct   3840
gctgccagtg gcgataagtc gtgtcttacc gggttggact caagacgata gttaccggat   3900
aaggcgcagc ggtcgggctg aacggggggt tcgtgcacac agcccagctt ggagcgaacg   3960
acctacaccg aactgagata cctacagcgt gagctatgag aaagcgccac gcttcccgaa   4020
gggagaaagg cggacaggta tccggtaagc ggcagggtcg gaacaggaga gcgcacgagg   4080
gagcttccag ggggaaacgc ctggtatctt tatagtcctg tcgggtttcg ccacctctga   4140
cttgagcgtc gatttttgtg atgctcgtca ggggggcgga gcctatggaa aaacgccagc   4200
aacgcggcct ttttacggtt cctggccttt tgctggcctt ttgctcacat gttctttcct   4260
gcgttatccc ctgattctgt ggataaccgt attaccgcct ttgagtgagc tgataccgct   4320
cgccgcagcc gaacgaccga gcgcagcgag tcagtgagcg aggaagcgga agagcgcctg   4380
atgcggtatt ttctccttac gcatctgtgc ggtatttcac accgcatatg gtgcactctc   4440
agtacaatct gctctgatgc cgcatagtta agccagtata cactccgcta tcgctacgtg   4500
actgggtcat ggctgcgccc cgacacccgc caacacccgc tgacgcgccc tgacgggctt   4560
gtctgctccc ggcatccgct tacagacaag ctgtgaccgt ctccgggagc tgcatgtgtc   4620
agaggttttc accgtcatca ccgaaacgcg cgaggcagca gatcaattcg cgcgcgaagg   4680
cgaagcggca tgcataatgt gcctgtcaaa tggacgaagc agggattctg caaaccctat   4740
gctactccgt caagccgtca attgtctgat tcgttaccaa ttatgacaac ttgacggcta   4800
catcattcac tttttcttca caaccggcac ggaactcgct cgggctggcc ccggtgcatt   4860
ttttaaatac ccgcgagaaa tagagttgat cgtcaaaacc aacattgcga ccgacggtgg   4920
cgataggcat ccgggtggtg ctcaaaagca gcttcgcctg gctgatacgt tggtcctcgc   4980
gccagcttaa gacgctaatc cctaactgct ggcggaaaag atgtgacaga cgcgacggcg   4040
acaagcaaac atgctgtgcg acgctggcga t                                  5071
```

METHOD FOR POOLED INTRON TAGGING FOR REAL TIME DRUG SCREENING

The present application is a national phase application under 35 U.S.C. § 371 of International Application No. PCT/EP2020/082295, filed Nov. 16, 2020, the entire contents of which are hereby incorporated by reference. International Application No. PCT/EP2020/082295 claims the priority benefit of European Application No. 19211077.3, filed Nov. 22, 2019.

This application contains a Sequence Listing, which has been submitted electronically as an ASCII text file and is hereby incorporated by reference in its entirety. Said Sequence Listing, created on Aug. 3, 2023, is named VOSSP0131US_ST25.txt and is 22,573 bytes in size.

The present invention relates to a method for monitoring the effect of an environmental factor on the proteome of a cell. Furthermore, cell populations are provided that comprise multiple cells each comprising an inserted tag sequence in an intron of said cell, wherein the tag is inserted in-frame with the preceding exonic sequence and wherein the intron into which the tag is inserted is different between cells.

While most currently available pharmacological agents, including small molecule pharmaceuticals or pharmacologically active biologics act as inhibitors of enzymes or as modulators of receptors and transporter, drugs may also exert other functions, like (but not limited to) the inhibition or induction of protein-protein interactions and the stabilization or degradation of target proteins.

Currently available methods for the unbiased discovery and for the elucidation of biological/pharmacological functions of bioactive compounds ("mechanisms of action") and/or some of the known screening methods of substances for their potential use pharmaceuticals are based on the monitoring of the biological and/or pharmacological effects on proteomes and transcriptomes; see, inter alia, Rix (2009) Nat Chem Biol 5, 616-24; Martinez Molina (2013) Science 341, 84-7; Savitski (2014) Science 346, 1255784; Drewes (2015) Trends Biotechnol 36, 1275-1286; Huber (2015). Nat Methods 12, 1055-7; Subramanian (2017). Cell 171, 1437-1452 e17; or Lamb (2006) Science 313, 1929-35.

Yet, costs and sample preparation requirements associated with these methods preclude their application in large scale screenings and/or they preclude the use of these methods on a large number of drugs/drug candidates at multiple concentrations and/or time points of assessment. Furthermore, other high-content screening approaches that monitor drug effects on cell morphology, as disclosed in Bray (2016) Nat Protoc 11, 1757-74 and/or protein localization approaches by microscopy, for example by staining of fluorescent-tagging approaches, are hampered by the fact that these methods merely allow the monitoring of one or of only a few selected proteins.

The prior art saw in this context approaches in which fluorescently tagged reporter cells are generated either by overexpression to non-physiologic levels, by targeting a single gene with a homologous recombination template. Also "genetrap" approaches have been applied in this context; see, e.g. Morin (2001) Proc Natl Acad Sci USA 98, 15050-5). Yet, such approaches are limited by integration site biases. Yet, these "genetrap virus approaches" employ viral constructs in order to generate tagged cell pools. Since the employed viruses have tremendous integration site biases, namely in the first intron, some genes are targeted much more efficiently by these vial constructs than others.

Furthermore, there are no means in these approaches to select specific gene sets or specific introns to be targeted.

Serebrenik and colleagues proposed a tagging technology of endogenous genes by homology-independent intron targeting, whereby intron-based protein trapping with homology-independent repair-based integration of a generic donor was combined, see Serebrenik (2019) Genome Research 29, 1322-28. The corresponding approach is based on homology-independent CRISPR-Cas9 editing to place a fluorescent tag as a synthetic exon into introns of individual target genes has been described by combining a generic sgRNA excising a fluorescent tag flanked by splice acceptor and donor sites from a generic donor plasmid with co-expression of a gene-specific intron-targeting sgRNA. Based on the fact that this technology employs generic donors, it is speculated that this technology would enable the generation of multiple fusion cell lines but that this would require the cloning of additional intron-targeting sgRNAs. Yet, from the technology as provided by Serebrenik, an efficient way to determine which cell expresses which protein is not feasible.

Accordingly, there is a need in the art to provide for means and methods for a characterization of factors influencing individual proteins comprised in the whole proteome whereby the whole proteome or at least a substantial part thereof is or can be assessed.

The technical problem is solved by the embodiments as characterized in the claims and as provided herein.

In a first aspect, the present invention relates to a method for monitoring the effect of an environmental factor on the proteome or parts thereof of a cell, the method comprising the steps of:

(a) selecting introns to be targeted in the genome of a cell;
(b) identifying guide RNA (gRNA) sequences suitable for inserting a tag in the selected introns in the genome of the cell;
(c) cloning identified gRNA sequences and tag sequence into transduction vectors;
(d) contacting a population of the cell with said vectors of (c) to integrate the tag of (b) into selected introns;
(e) exposing cell population to environmental factor; and
(f) monitoring the effect of the environmental factor on the proteome based on the detection of the tag prior to exposure of the cell population to the environmental factor and subsequent to exposure of the cell population to the environmental factor.

In a second aspect, the present invention relates to a method for monitoring the effect of an environmental factor on the proteome or parts thereof of a cell, the method comprising the steps of:

(a) selecting introns to be targeted in the genome of a cell;
(b) identifying guide RNA (gRNA) sequences suitable for inserting a tag in the selected introns in the genome of the cell;
(c) cloning identified gRNA sequences and tag sequence into vectors;
(d) contacting a population of the cell with said vectors of (c) to integrate the tag of (b) into selected introns;
(e) exposing cell population to environmental factor; and
(f) monitoring the effect of the environmental factor on the proteome based on the detection of the tag prior to exposure of the cell population to the environmental factor and subsequent to exposure of the cell population to the environmental factor preferably wherein in step (c) the identified gRNA sequences are cloned into a transduction vector and the tag sequence is cloned into a donor plasmid or minicircle DNA.

Accordingly, within the present invention, the tag sequence may be cloned into a donor plasmid or minicircle DNA which is then used as vector for transduction. Accordingly, the term "cloning identified gRNA sequences and tag sequence into transduction vectors" as used herein is to be understood as comprising the cloning into a donor plasmid or minicircle DNA as a vector.

As shown in the appended examples, the methods of the present invention comprise a step of identifying gRNA sequences suitable for inserting a tag in introns in the genome of a cell. In the methods of the present invention, it is preferred that a cell comprised in a population of cells that is to be tagged receives a single tag. The general principle of intron tagging is described by Serebrenik et al. (2019), loc cit. The strategy of Serebrenik et al. relies on a single generic sgRNA excising a single fluorescent tag flanked by splice acceptor and donor sites from a generic donor plasmid, which is co-expressed with a single gene-specific intron-targeting sgRNA specifying the single integration site.

However, as shown in the appended examples, the methods of the present invention generate an intron-tagged cell pool that is then used to characterize/monitor effects of an environmental factor on the proteasome or parts thereof of a cell type. This is achieved by tagging cells in a population of cells of the same cell type, whereby each cell receives a single tag. The population thus comprises cells tagged at different genomic sites, providing as a whole a tagged proteome or tagged parts thereof. Accordingly, and in contrast to the technology as provided by Serebrenik et al. (2019), loc cit., the present invention provides for means and methods wherein the whole proteome (or at least substantial parts thereof) can be monitored in one individual cell population. Therefore, the present invention provides for a "one shot" analysis of the whole proteome (or substantial parts thereof). As such, the present invention, for the first time, allows the analysis of the whole proteome (or at least substantial parts thereof) in one experiment by using different gRNA sequences for a multitude of tagged proteins combined with in situ sequencing. In this regard, the inventors found that the use of a sequencing-enabling vector that expresses the gRNA as part of the transcript that can be detected by in situ sequencing, such as a CROPseq vector, as a transduction vector allows the identification of the individual gRNA sequence, which corresponds to the tagged protein in each clone in the pool, e.g. using an imaging technique such as microscopy.

While most currently available pharmacological agents, including small molecule pharmaceuticals or pharmacologically active biologics act as inhibitors of enzymes or as modulators of receptors and transporters, drugs may also exert other functions, like (but not limited to) the inhibition or induction of protein-protein interactions and the stabilization or degradation of target proteins. In context of this invention, a scalable strategy to discover in real time the effects drugs exert on levels and subcellular localizations of a large subsets of the proteome is provided. Illustratively for the present invention, CRISPR-Cas9 based intron tagging was employed to generate cell pools expressing hundreds of GFP-fusion proteins at endogenous levels, monitor drug effects on protein levels and localization by time-lapse microscopy, and identify targeted introns by in situ sequencing. This is also documented in the appended figures and examples. From the pool of tag-positive cells (here illustratively GFP positive cells), more than 500 individual clones are isolated and these positive cells where analyzed/imaged by fluorescence microscopy in order to reveal the subcellular protein localization of many proteins for which the subcellular protein localization had not been previously characterized. Furthermore, the inventive pool of cells may also be used to study protein dynamics in response to various metabolic perturbations either in an arrayed or pooled format and strategies to identify individual drug-responsive clones in the pool are provided.

As disclosed herein, the present invention provides for methods for monitoring the effect of an environmental factor on the proteome or parts thereof of a cell. In context of this invention, the term "part(s) of the proteome" relates to a substantial part of the proteome, i.e. at least 100, at least 200 at least 300 at least 400 at least 500, at least 600, at least 700 and more preferably at least 900 expressed genes (coding for proteins).

In particular and in contrast to the prior art, in particular Serebrenik et al., the invention provided herein allows scalability to enable pooled protein tagging of a multitude of metabolic enzymes and epigenetic modifiers. As shown in the appended Examples, more than 900 metabolic enzymes were targeted. Exposing the GFP-tagged cells to compounds to monitor drug effects on the localization and levels of hundreds of proteins in real time in a pooled format, followed by identification of responding clones by in situ sequencing of the expressed intron-targeting sgRNA that corresponds to the tagged protein, as shown in FIG. 2*a*, represents a major advantage over methods of the prior art.

It is preferred that the methods of the present invention further comprise a sequencing step subsequent to step (d).

As detailed above, the sequencing step allows the association of individual cells with tagged proteins by sequencing the individual gRNA. This may be achieved by sequencing the gRNA insert while it is not necessary to sequence the protein directly. This can either be done on whole population level or based on expressed proteins, for example subsequent to a cell sorting step based on the expressed tag. Accordingly, in the methods of the present invention, the gRNA insert, or a part thereof, of (a) cell(s) of the population is sequenced in the genome of said cell(s) or in the transcriptome of said cell(s).

In a further preferred embodiment, the sequencing step is subsequent to step (f) of the methods of the invention.

Sequencing of the gRNA insert in the transcriptome preferably further comprises a step of reverse transcription and the use of a sequencing vector as transduction vector. An exemplary vector suitable for sequencing is a Crop-Seq vector. In an exemplary embodiment, the procedure may be as in FIG. 2*c*. The method may be further adapted by using in situ sequencing using the Illumina NextSeq 500/550 kit v2, which provides a two-color system compatible with the GFP expressing cells.

As shown in the appended examples, the introns to be targeted are selected based on the reading frame of the upstream exonic sequence, wherein the to be inserted sequence is in-frame with the exonic sequence. As shown in FIG. 2*b*, designing the intron targeting library required the inventors to analyze the target gene set regarding the number of available introns (FIG. 2*b*) and whether the introns were in the right reading frame (only one out of 3 reading frames is suitable to generate functional GFP integrations). Based on these criteria 14,146 sgRNA sequences for 11,614 introns in 2.390 genes were generated. Furthermore, the introns to be targeted can be comprised in genomic sequences of metabolic enzymes, chromatin proteins, kinases, genes coding for proteins in the ubiquitin/proteasome pathways, transcription factors, ion channels, transporters, receptors or at least one intron per protein coding gene in the genome can be targeted.

Design of sgRNA sequences is further based on cutting efficiency. Thus, in a further embodiment, the gRNA sequences suitable for inserting a tag in the selected introns in the genome of the cell are identified according to cas9 cutting efficiency or Cpf1 cutting efficiency or Cas12b cutting efficiency. Additionally, or alternatively, the gRNA sequences suitable for inserting a tag in the selected introns in the genome of the cell are identified according to their occurrence in the genome of the cell, preferably wherein the occurrence is 1.

The vector further encodes for a tag that is to be inserted into the intron. The tag can be any tag allowing detection subsequent to integration or expression. Preferably, the tag is a fluorescence tag (preferably green fluorescent protein (GFP or enhanced GFP) or yellow fluorescent protein (YFP), or red fluorescent protein (RFP) or a tag suitable for detection by covalent (e.g. Halo tag, Clip tag, Snap tag) or non-covalent (e.g. Strep-tag, HA tag, dTag) binding to a detection reagent enabling detection by microscopy by fluorescence or luminescence.

Once the sgRNA sequences and the tag sequences have been selected and cloned, the library of sgRNA vectors is contacted with a population of a cell to integrate the tag of into selected introns.

To ensure that each cell gets infected only with a single vector and thus only one intron-targeting sgRNA, cells are preferably infected at a multiplicity of infection of below 1, preferably 0.8, 0.6, 0.4, more preferably 0.2. The term “multiplicity of infection” is to be understood as meaning that only 80%, 60%, 40% or 20%, respectively, of the cells are infected.

In order to select for infected cells, a selection marker can be comprised in the vector. An exemplary marker is the puromycin selection marker also present on the vector, e.g. the CROP-seq vector.

In an exemplary method, transient transfection can subsequently be used to introduce a plasmid for expression of Cas9 (that would introduce a cut specifically in one intron as specified by the sgRNA/gRNA previously introduced to the same cell with the CROP-seq vector) and a generic sgRNA/gRNA. A second plasmid can also be introduced that acts as a generic donor plasmid that provides the tag sequence, for example an EGFP sequence, to be integrated into the intron. This plasmid contains a Cas9 cut-site (targeted by the generic sgRNA sequence present on the Cas9 plasmid), a splice acceptor site, tag sequence (e.g. EGFP), a splice donor site and another Cas9-cut site (targeted by the generic sgRNA sequence present on the Cas9 plasmid). As an alternative to the generic donor plasmid with two Cas9 cut-sites, minicircle DNA that does not comprise a plasmid backbone and a single Cas9 cut-site, a splice acceptor site, tag sequence (e.g. GFP or EGFP) and a splice donor site may be used. When using a minicircle, the intron tagging efficiency is increased, due to the lack of a plasmid backbone that can get integrated at the intronic integration site instead of the tag sequence containing fragment. The methods may further comprise selection for cells that are successfully transfected (e.g. blasticidin marker on the Cas9 plasmid) and expansion of the cells, for example over a period of 5 days.

The methods of the present invention may further comprise a step of separating tagged cells from non-tagged cells. The separation method depends on the tag that is used. In a preferred embodiment, the cells are fluorescence tagged and the cells are separated using FACS. Accordingly, FACS or an alternative separation method can be used to sort out targeted cells. In addition, tagged proteins can be selected according to expression levels. That is, all proteins are expressed at endogenous levels, and some proteins are expressed to very low levels. To differentiate between expression levels, a further parameter may be used (e.g. a further channel during selection), e.g. for cell-specific background fluorescence and sort cells that are enriched for the tag, for example GFP or EGFP (FIG. 2*c*).

The sorted pool of tagged cells or the unsorted pool comprising tagged cells may further be characterized using a suitable method based on the introduced tag. For example, protein expression, protein localization, surface expression, protein-protein interaction, protein stability, and/or protein mobility may be monitored using a suitable detection method.

As such, the invention also relates to a population of cells comprising multiple cells each comprising an inserted tag sequence in an intron of said cell, wherein the tag is inserted in-frame with the preceding exonic sequence and wherein the intron into which the tag is inserted is different between cells.

As detailed above, the cells may also be characterized by sequencing. In one exemplary embodiment, the intron tagged cell pool can be characterized by PCR amplifying the integrated sgRNA sequence from genomic DNA, next generation sequencing and mapping back to the sequences in the designed sgRNA library. This way it was determined that more highly expressed genes were more likely to be successfully tagged (FIG. 2*e*).

In a further exemplary embodiment, the intron tagged cell pool can be further characterized by diluting to single cells and growing them up to large colonies on a 96-well plate. These single-cell derived clones can be characterized by imaging (FIG. 2*f*.) to identify the targeted protein again by PCR amplifying the integrated sgRNA sequence from genomic DNA, next generation sequencing and mapping back to the sequences in the designed sgRNA/gRNA library. This way it could be confirmed that the vast majority of cells indeed harbor only a single tagged protein. Furthermore, it was observed that the vast majority of protein locations in the clones corresponded to those identified by antibody-based staining of the targeted protein in the Human Cell Atlas (FIG. 2*g*).

Figure 6:
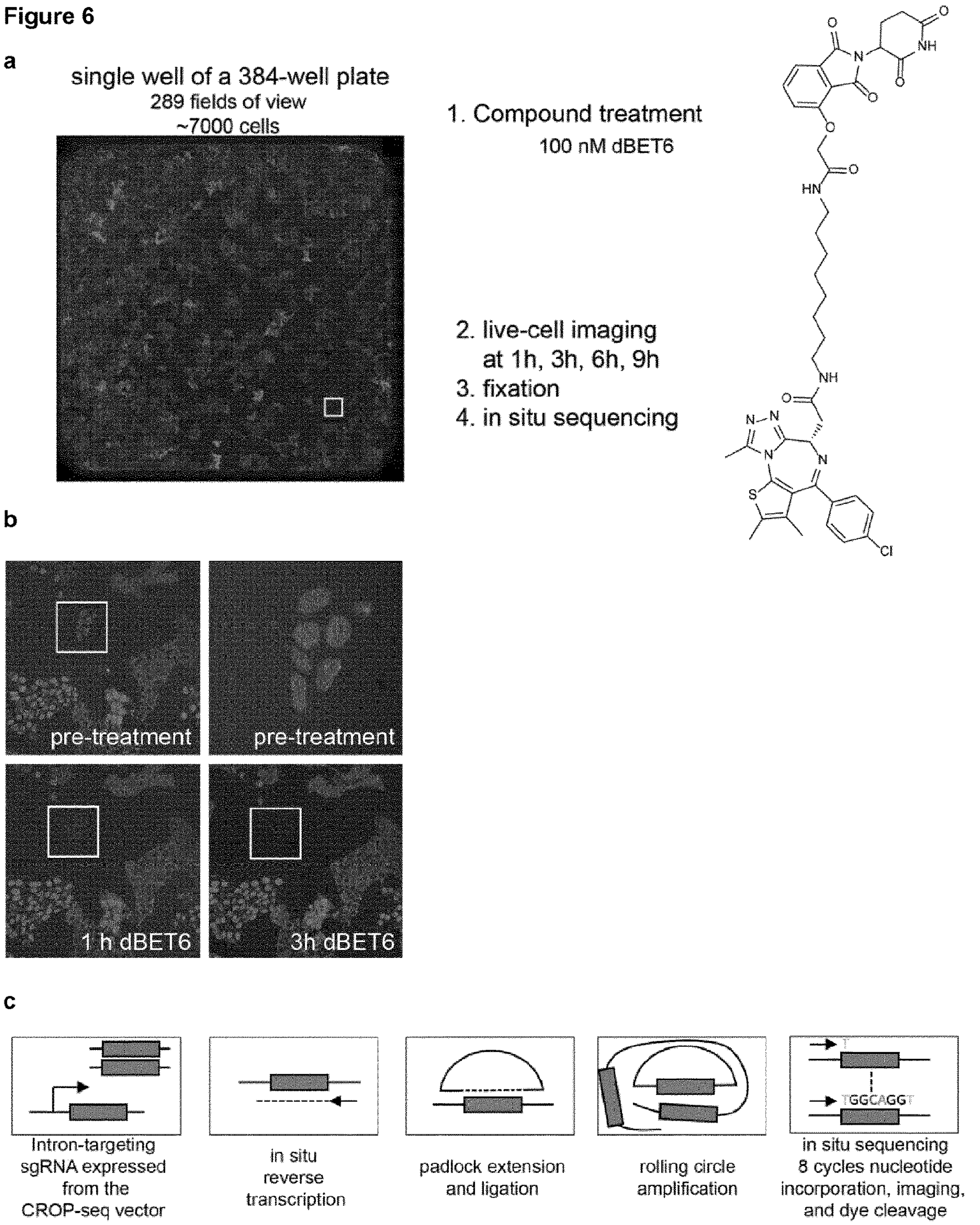
Figure 6:
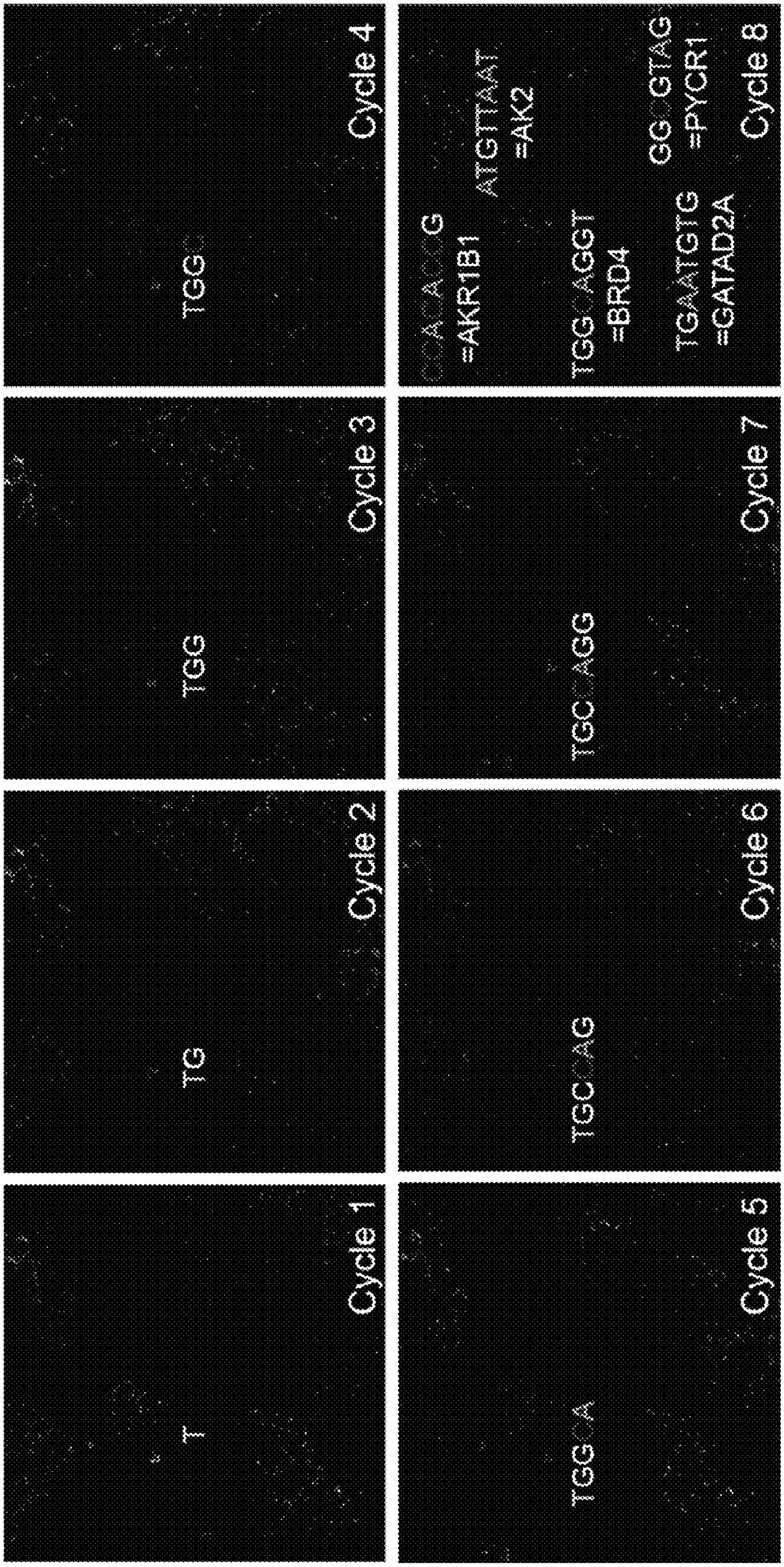
Figure 6:
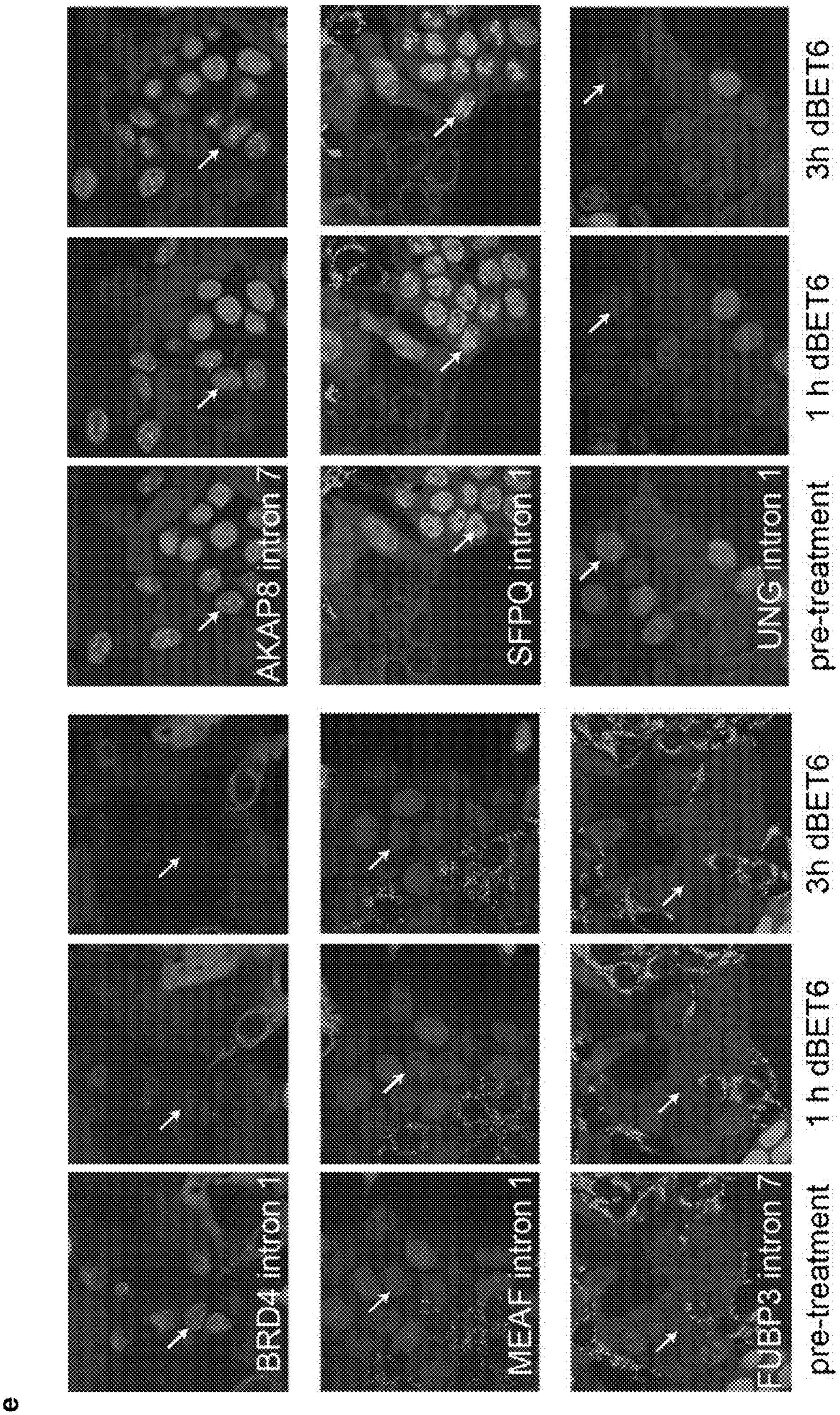

It is thus an object of the present invention to monitor effects of environmental factors on the proteome or parts thereof of a cell. The environmental factor may be selected from radiation, a chemical compound, a biological compound, temperature, nutrient depletion, ion concentrations or combinations thereof. In an exemplary embodiment, the method may comprise plating of cell pools at conditions of approximately 7,000 cells per well in a 384-well plate (FIG. 6*a*). While the method works for a single cell per tagged protein, it is preferred to have at least 5 cells per tagged protein for robustness. An image from the cell pool before compound treatment is taken. Subsequently, the cells are exposed to the environmental factor, for example by adding a chemical compound. The chemical compound may be a drug, a small molecule, an siRNA, an shRNA/sgRNA virus, a protein. In one embodiment, the environmental factor may be at different intensities/concentrations for different cell populations, for example to obtain dose-response curves. Subsequently, at least one further image is taken. However, multiple images may be taken in order to follow the effect on the time scale. For example, images may be taken after 1 h, 3 h,6 h,9 h, but this timeframe can be freely adjusted (FIG. 6*b*).

Within the present invention, the cell may be a HAP1 cell, K562 cell, HeLa cell, KBM7 cell, BT474 cell, MG-63 cell, SKNAS cell, A427 cell, A375 cell, A498 cell, RCH-ACV cell, HEK293T cell, A673 cell, SK-N-MC cell, A549 cell, SKMES1 cell, NCIH727 cell, THP1 cell, NB4 cell, MOLM13 cell, KASUMI-1 cell, HEL cell, NB-4 cell, HL-60 cell, RS4-11 cell, MOLT7 cell, aTC1 cell, bTC3 cell, Min6 cell or another cell line, preferentially an adherent, non-migratory cell line.

The invention furthermore relates to a population of cells comprising multiple cells each comprising an inserted tag sequence in an intron of said cell, wherein the tag is inserted in-frame with the preceding exonic sequence and wherein the intron into which the tag is inserted is different between cells. Accordingly, the present invention provides for a novel and inventive cell population that is characterized in that said cell population and that comprises multiple cells each individually tagged in one intron sequence of a gene coding for an (expressed) protein. As such the population of cells of the present invention provides a novel and inventive tool for whole proteome analysis as well as for a valuable tool for drug screenings on a cellular basis. In a further embodiment, the present invention comprises a kit comprising said novel and inventive cell population.

Such a kit is also particularly useful as means for drug screenings, drug evaluations, treatment monitoring, as research tool for basic sciences. Further uses of the inventive cell population are within the capabilities of the skilled artisan.

In a preferred embodiment, the population of cells of the present invention is obtained by a method comprising the steps of:

(a) selecting introns to be targeted in the genome of a cell;
(b) identifying guide RNA (gRNA) sequences suitable for inserting a tag in the selected introns in the genome of the cell;
(c) cloning identified gRNA sequences and tag sequence into vectors, preferably wherein the gRNA sequences are cloned into transduction vectors and the tag sequence is cloned into a donor plasmid or minicircle DNA;
(d) contacting a population of the cell with said vectors of (c) to integrate the tag of (b) into selected introns; and
(e) obtaining the population of cells.

The population of cells provided herein and, in particular, as obtained by the method of the invention, can be used e.g. for screening purposes, in particular drug screening. For example, the population of cells may be used in a method for screening a drug for its effect on the proteome of the cell population. This may be used, inter alia, in the screening of a drug suitable for downregulating/upregulating a specific protein or group of proteins that is/are part of the proteome of the population of cells.

The invention is further illustrated by the following non-limiting figures and examples:

FIG. 1: Many cytoplasmic and mitochondrial metabolic enzymes are found in the nucleus. The subcellular localization of some metabolic enzymes changes during the cell cycle or in response to perturbations. Protein localization of can be studied by immunofluorescence staining or by endogenously tagging proteins on the N- or C-terminus. (Figure from Berger and Sassone-Corsi (2016), Cold Spring Harb Perspect Biol 8:a019463)

Figure 2:
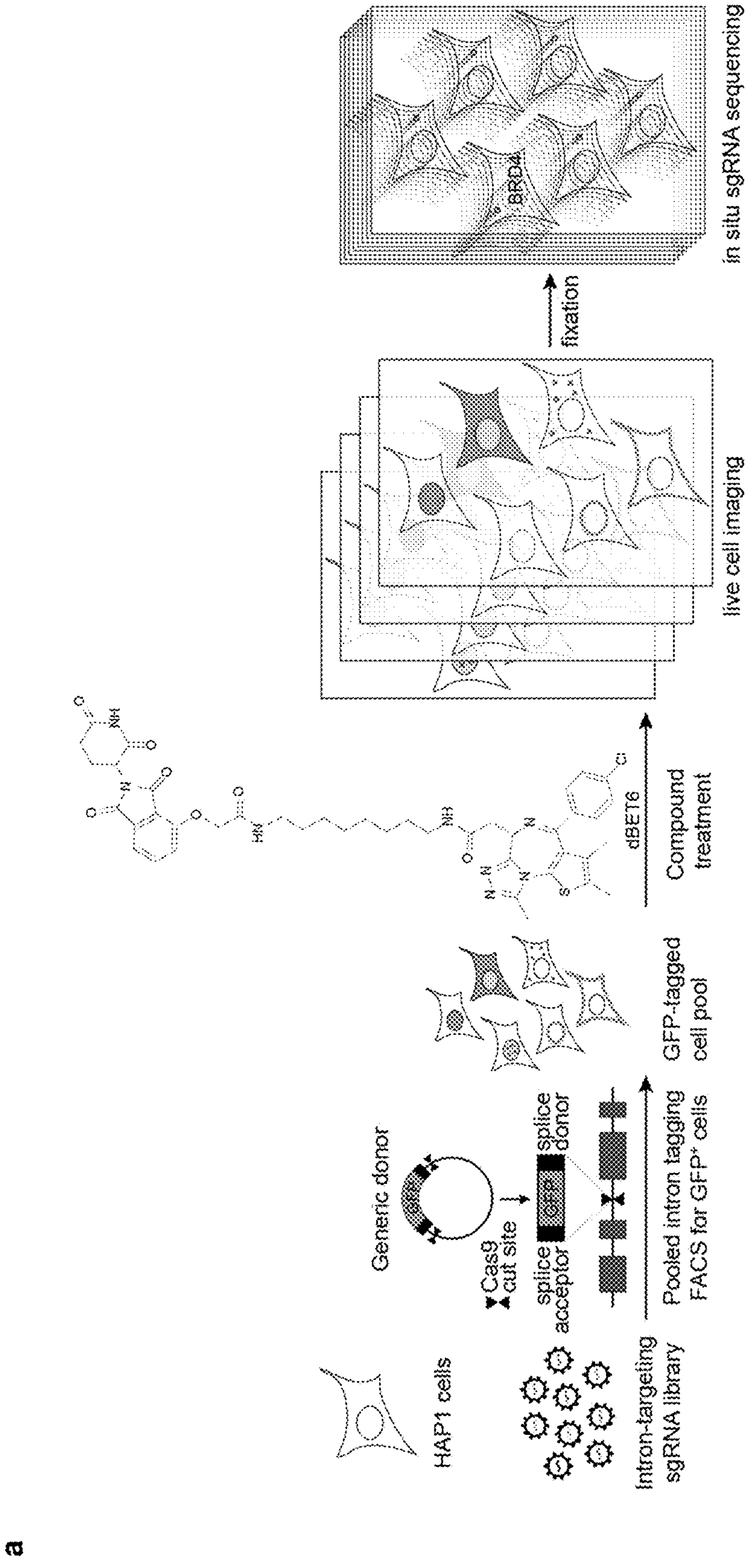
Figure 2:
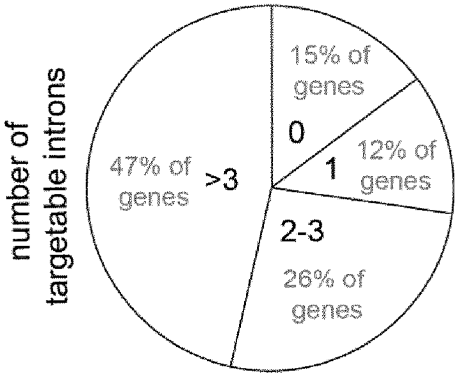
Figure 2:
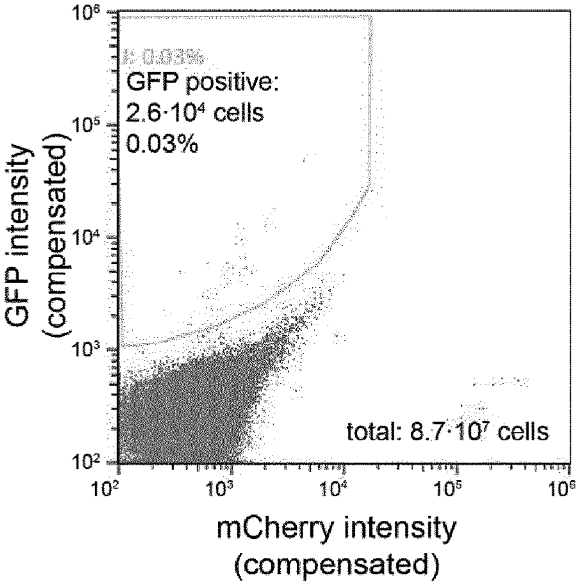
Figure 2:
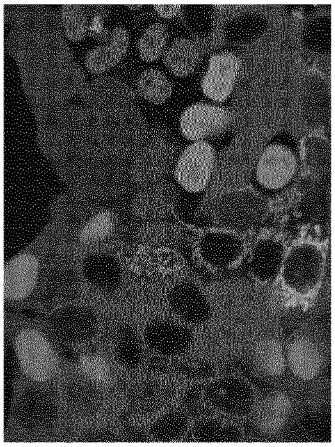
Figure 2:
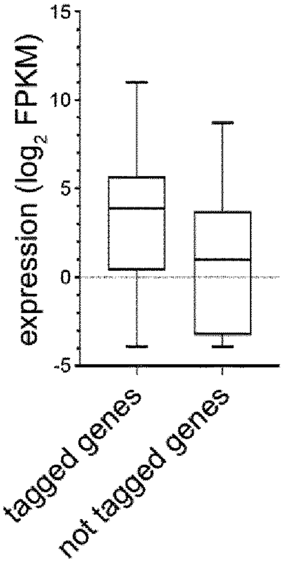
Figure 2:
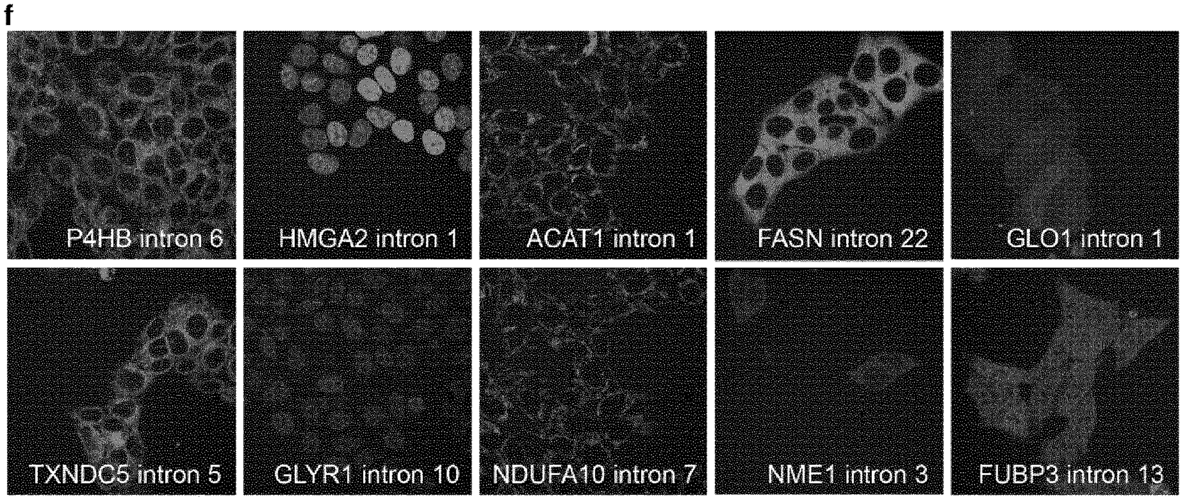

FIG. 2: Pooled GFP intron-tagging of metabolic enzymes. a. Schematic outline of the approach. b. Identification of targetable introns within metabolic genes. c. FACS sorting of clones with successful GFP-tagging by signal enrichment over background mCherry intensity. d. Representative image of sorted GFP-tagged cell pool. e. Comparison of RNA-seq expression in HAP1 cells between genes for which GFP-tagged cells could be isolated and genes that were targeted in the sgRNA library but did not result in successful clone isolation. f. Representative images of individual clones isolated by single cell dilution and identified by sgRNA NGS. g. Comparison of localizations of 335 individually isolated clones to localization annotations in the Human Protein Atlas.

Figure 3:
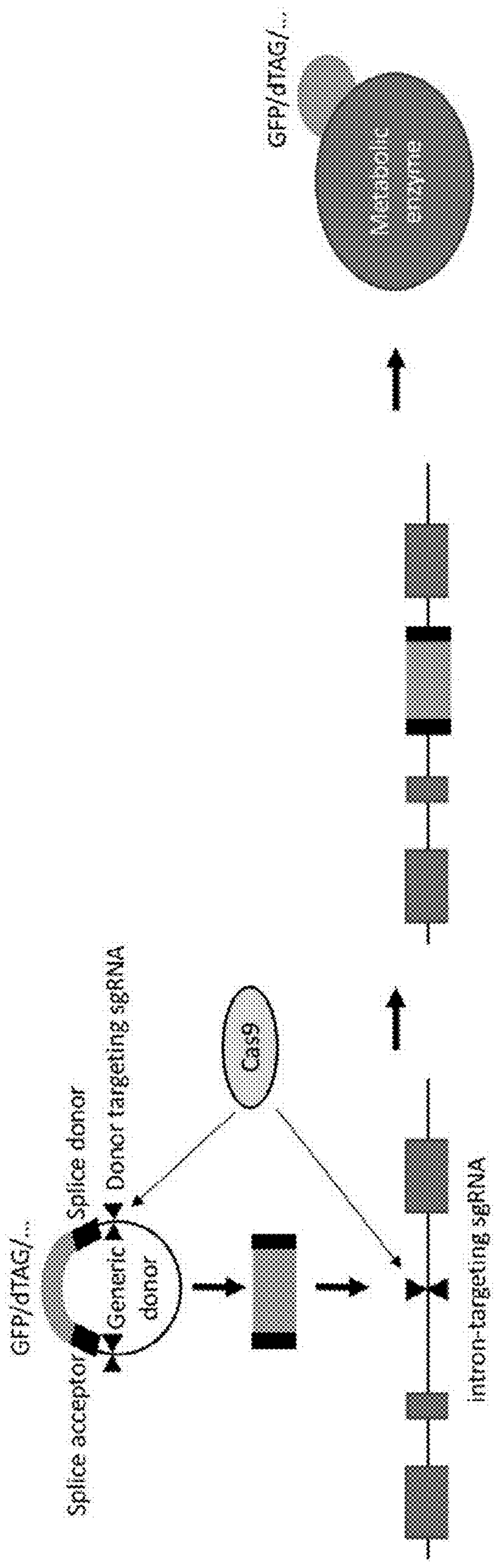
Figure 3:
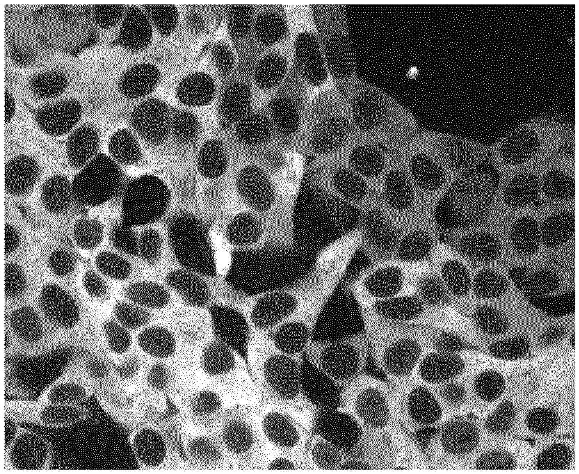

FIG. 3: Knock-in of a protein tag using an intron targeting strategy. a. Intron-tagging strategy with an intron targeting sgRNA, and a generic sgRNA targeting a donor plasmid targeting that provides a synthetic exon with the protein tag. This synthetic exon without homology arms is integrated into the intronic target site specified by the specific sgRNA via more NHEJ. This is a scalable targeting strategy as the same generic donor can be applied for all targets. b. Representative image confirming successful targeting of intron 26 in MTHFD1 with 2.2% efficiency.

Figure 4:
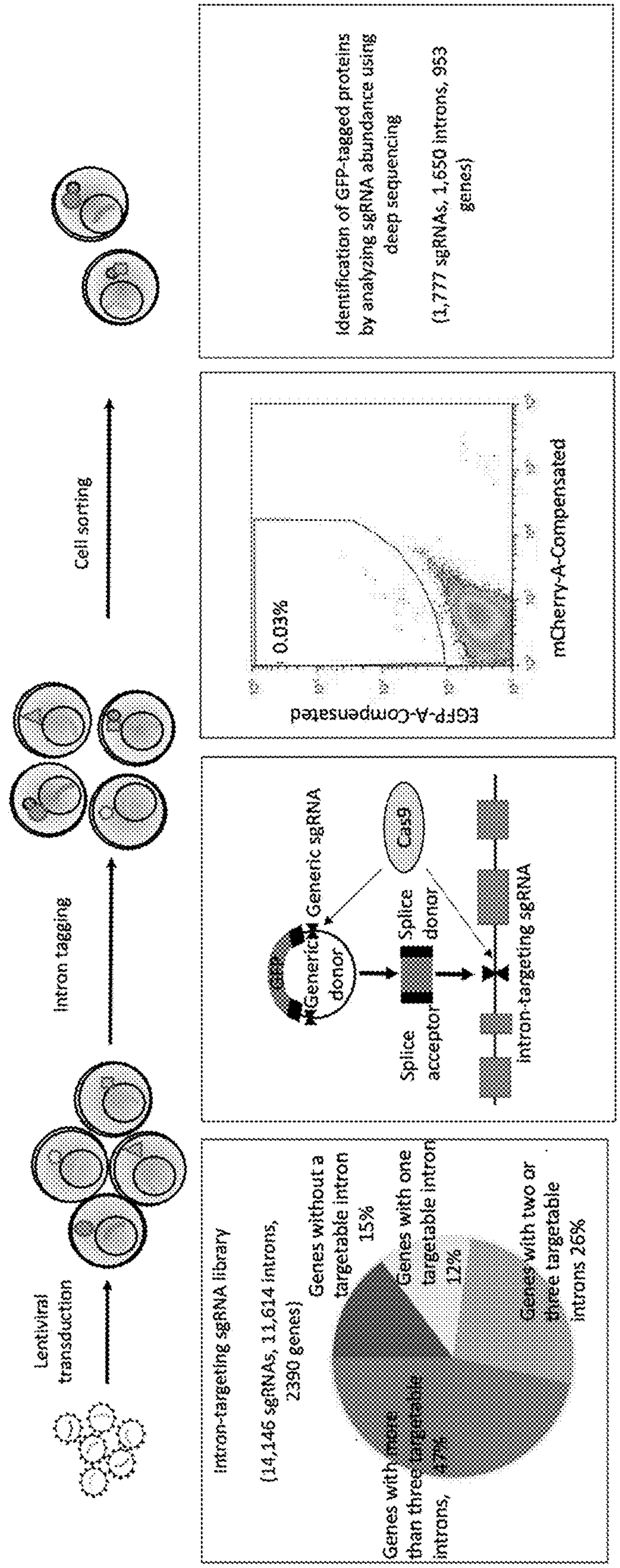
Figure 5:
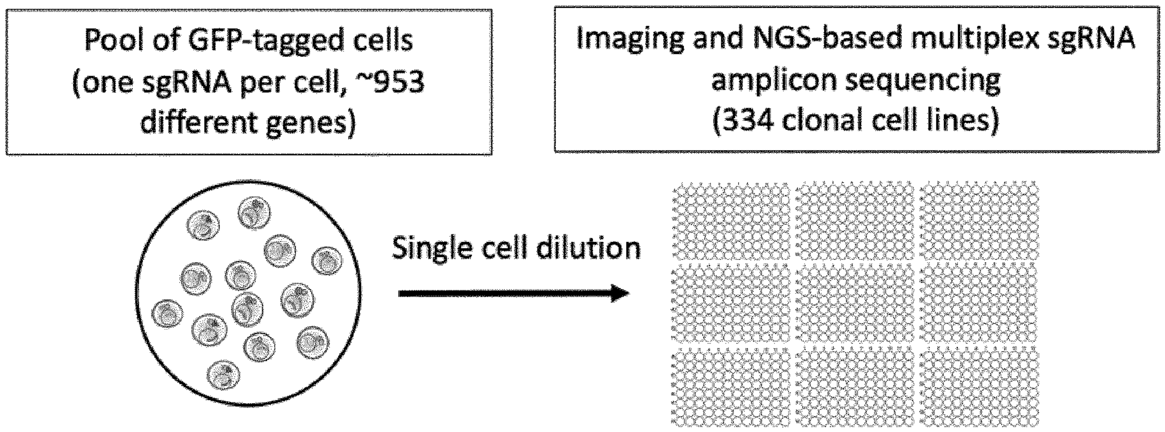
Figure 5:
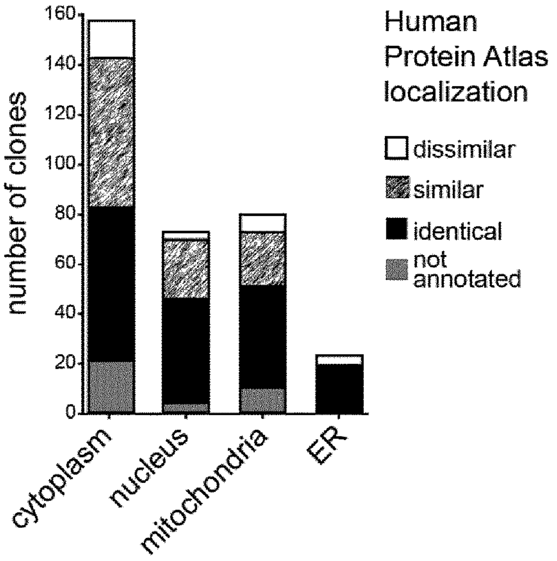

FIG. 4: Pooled protein-tagging of metabolic enzymes and epigenetic modifiers FIG. 5: Isolation of 334 clonal cell lines and comparison of subcellular protein localization to The Human Protein Atlas. a. Single cell cloning approach by single cell dilution to 96-well plates. b. Comparison of localizations of 335 individually isolated clones to localization annotations in the Human Protein Atlas. c. Representative images for the first 16 clones alphabetically FIG. 6: Compound screening on cell pools followed by in situ sequencing enables the detection of protein-specific compound effects. a. Stitched image of 289 fields of view representing an entire well on a 384-well plate containing approximately 7,000 individual cells. b. Identification of a clone with rapid loss of GFP signal following treatment with 100 nM dBET6, while neighboring clones are unaffected. c. Outline of the in situ sequencing approach. d. Images from 8 cycles in situ sequencing of the area shown in panel b. e. Selected images for clones showing localization changes following dBET6 treatment.

Figure 7:
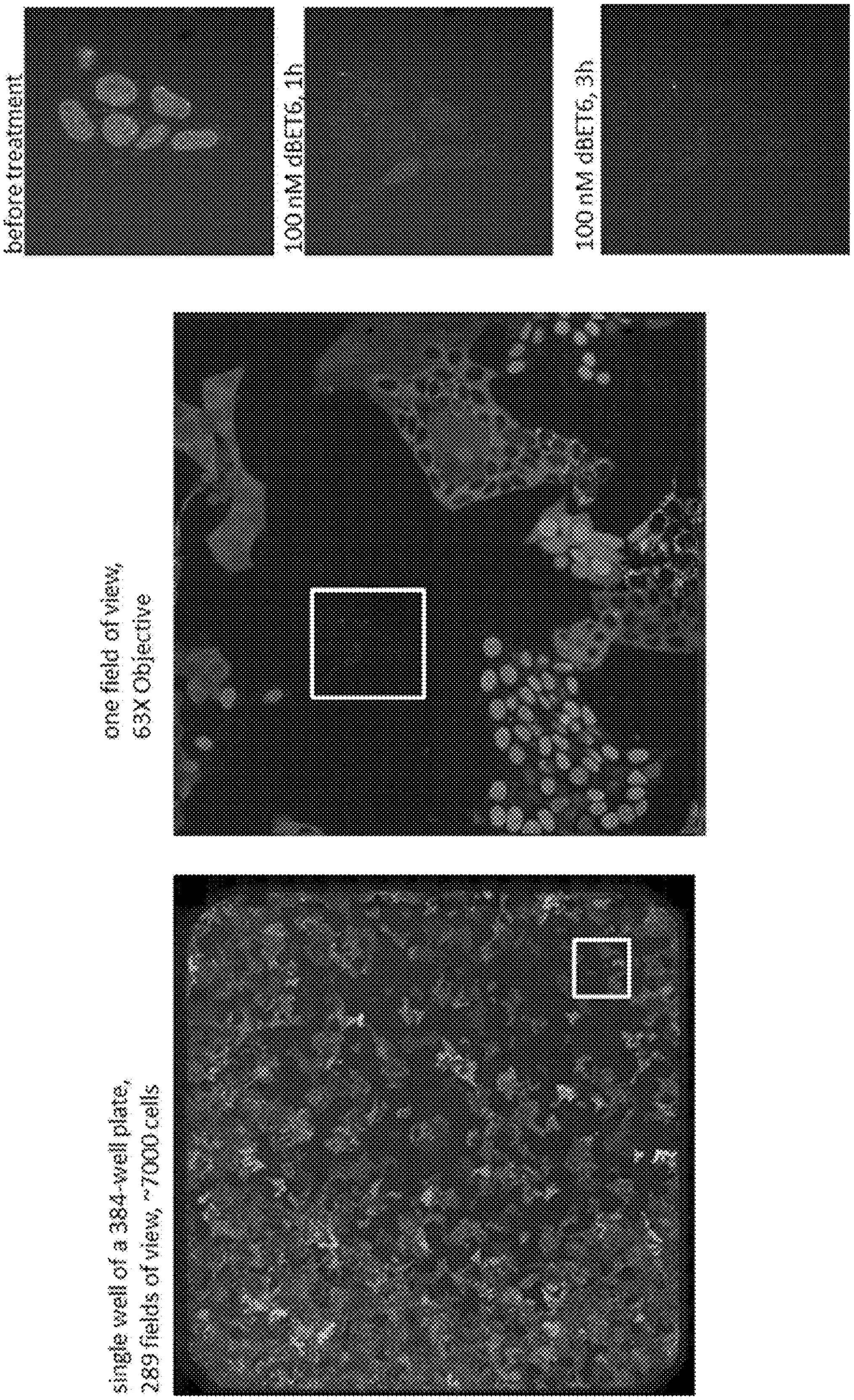

FIG. 7: Pooled screening approach to study drug effects on protein levels and localization.

Figure 8:
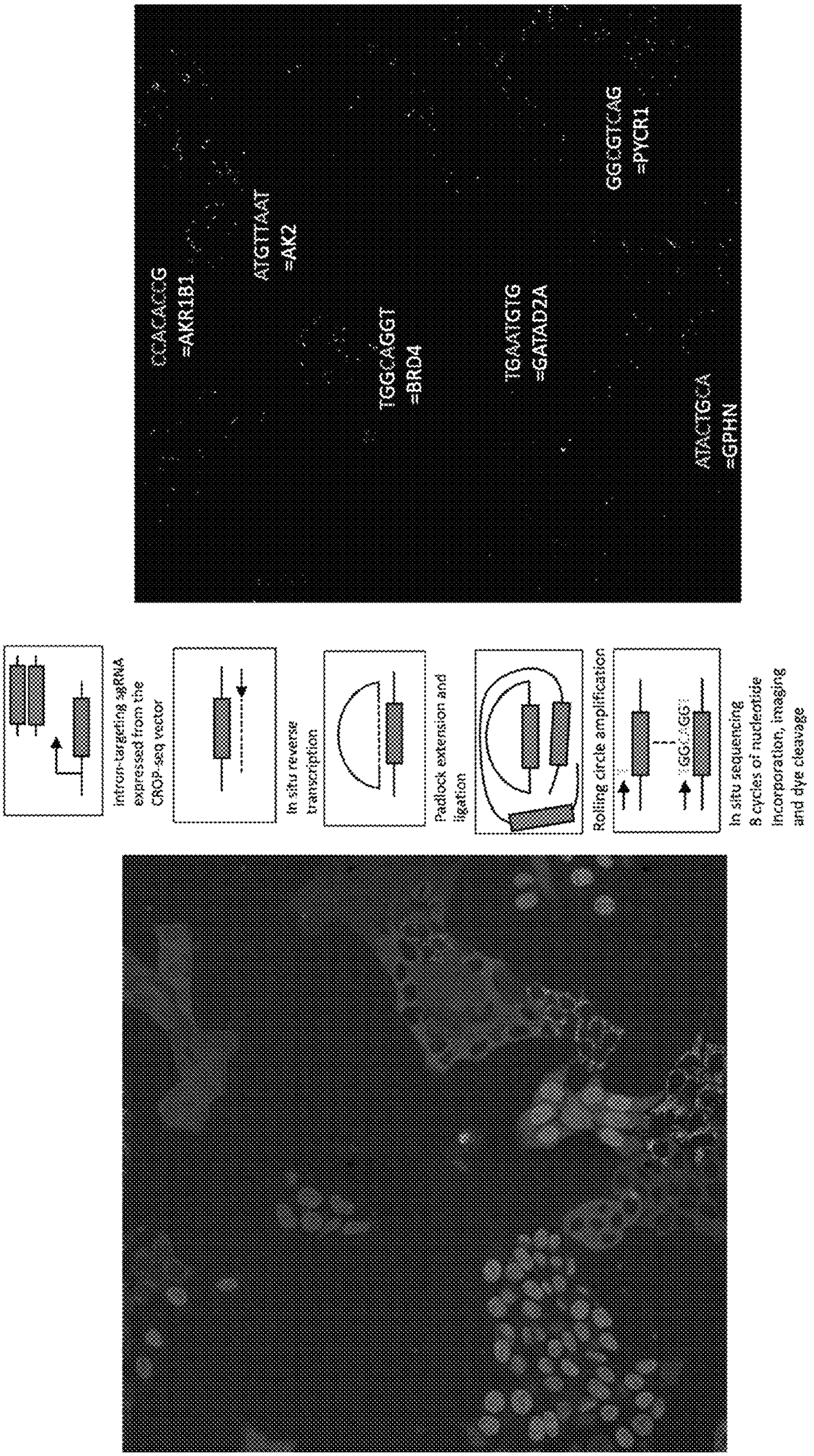

FIG. 8: In situ sequencing to identify the tagged protein in individual clones.

Figure 9:
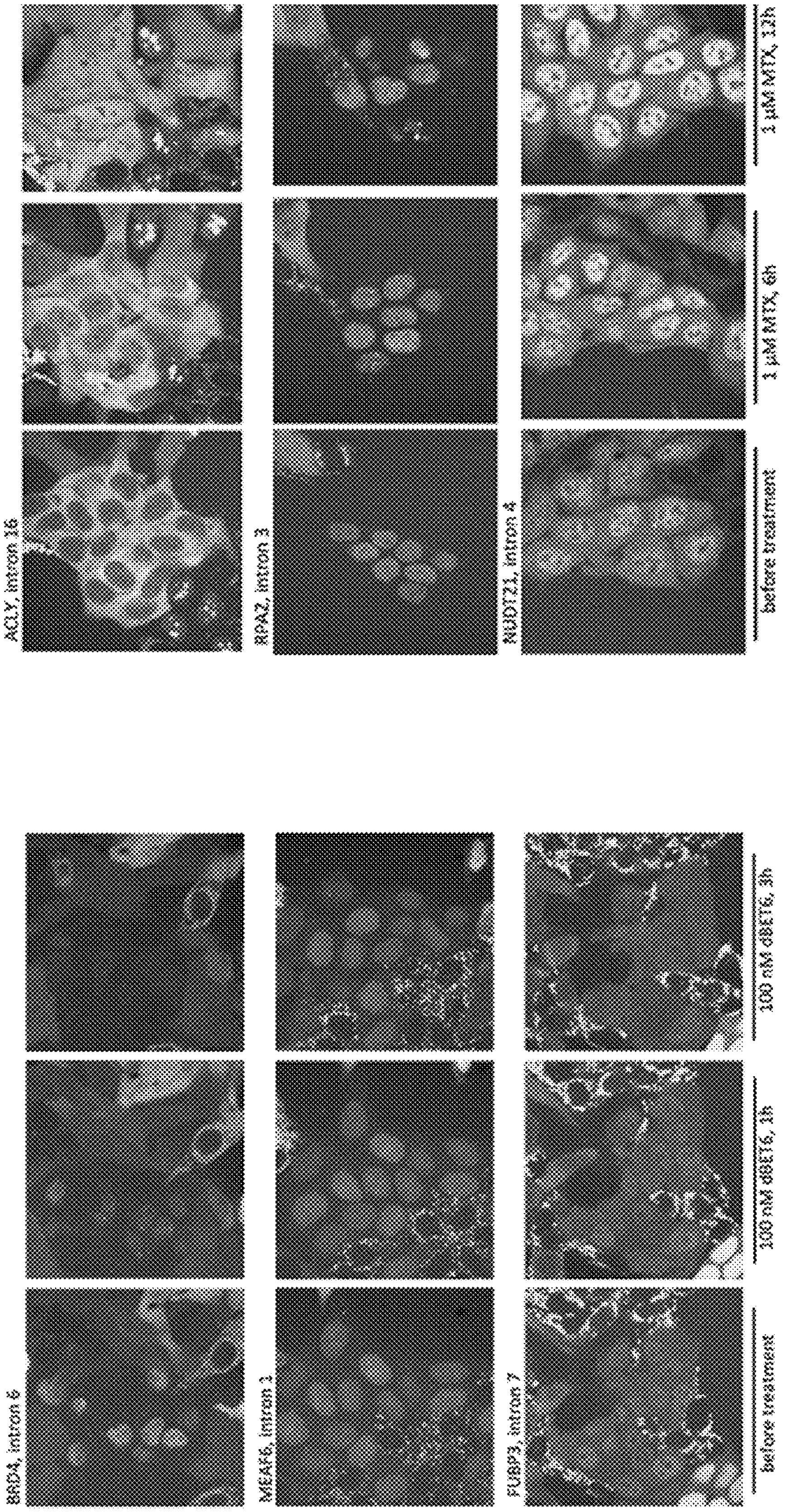

FIG. 9: Effects on protein localization and levels induced by the BRD4 degrader dBET6 and methotrexate.

Figure 10:
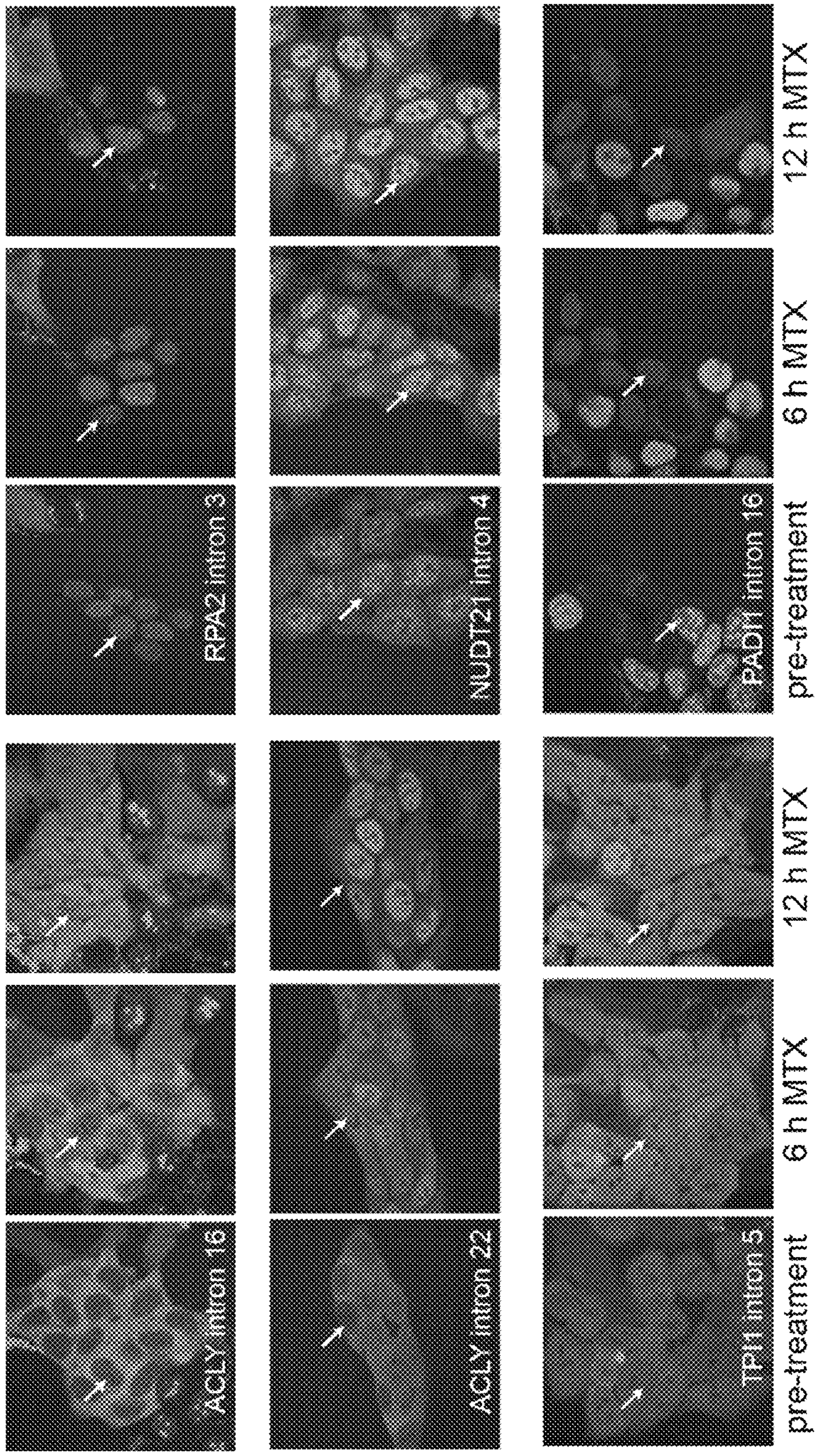
Figure 10:
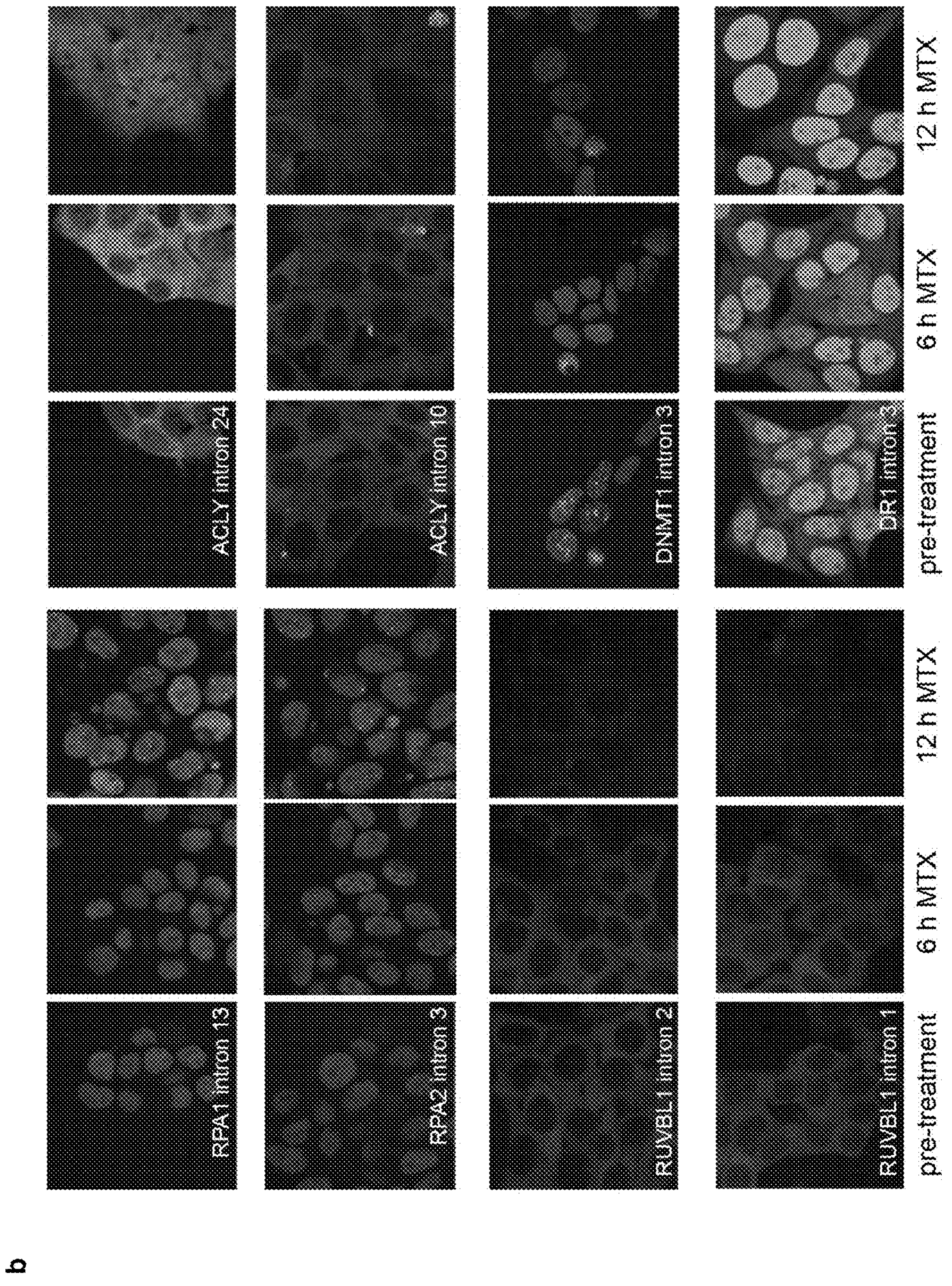

FIG. 10 Time-dependent changes in protein localization and levels following treatment with 1 μM methotrexate. a. Selected images showing changes following methotrexate treatment in cell pools, annotated by clone identification from in situ sequencing. b. Selected images showing changes in 335 arrayed clones exposed to methotrexate.

Figure 11:
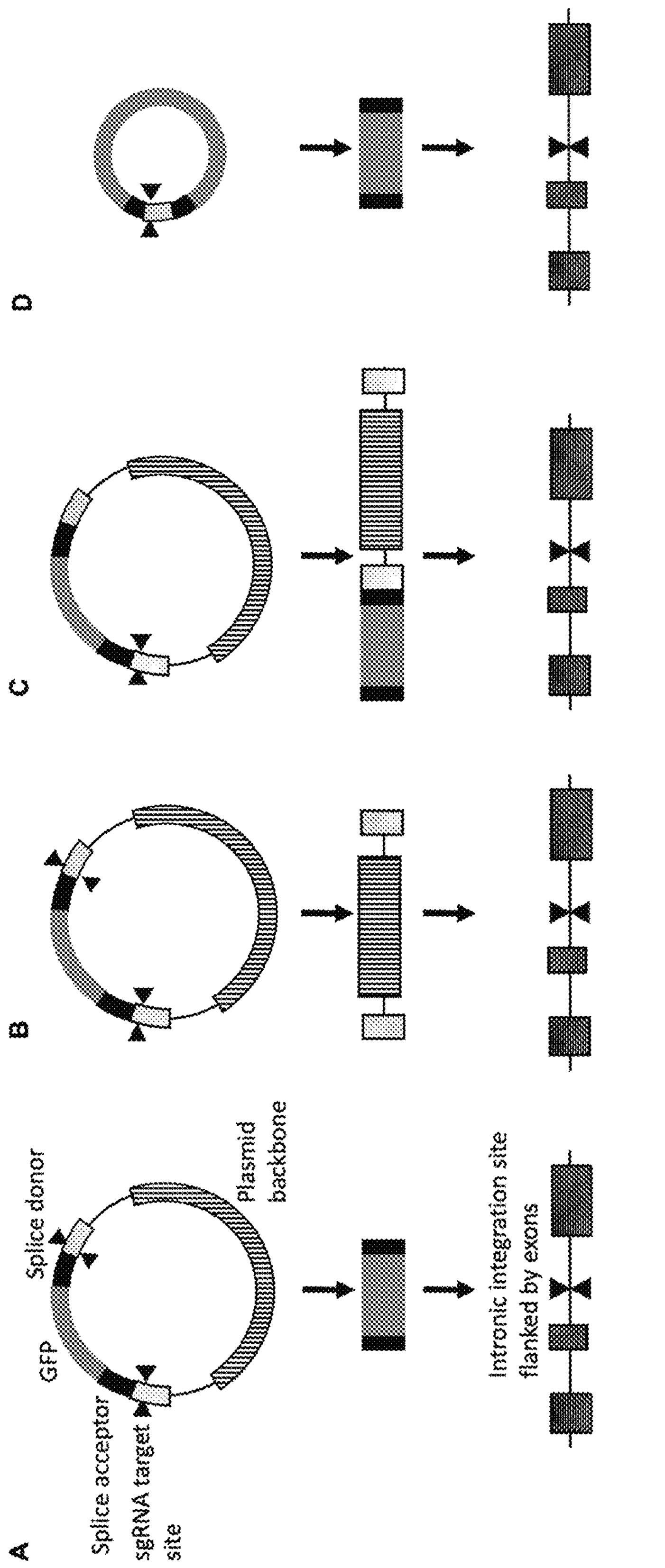

FIG. 11A. The GFP donor plasmid is cut at two sgRNA targeting sites followed by integration of a fragment containing GFP flanked by splice acceptor and splice donor sites. B. The plasmid backbone gets integrated instead of the GFP containing fragment. C. The GFP donor plasmid is cut only once and the entire plasmid gets integrated. D. A minicircle has only one sgRNA target site and no plasmid backbone can get integrated.

Figure 12:
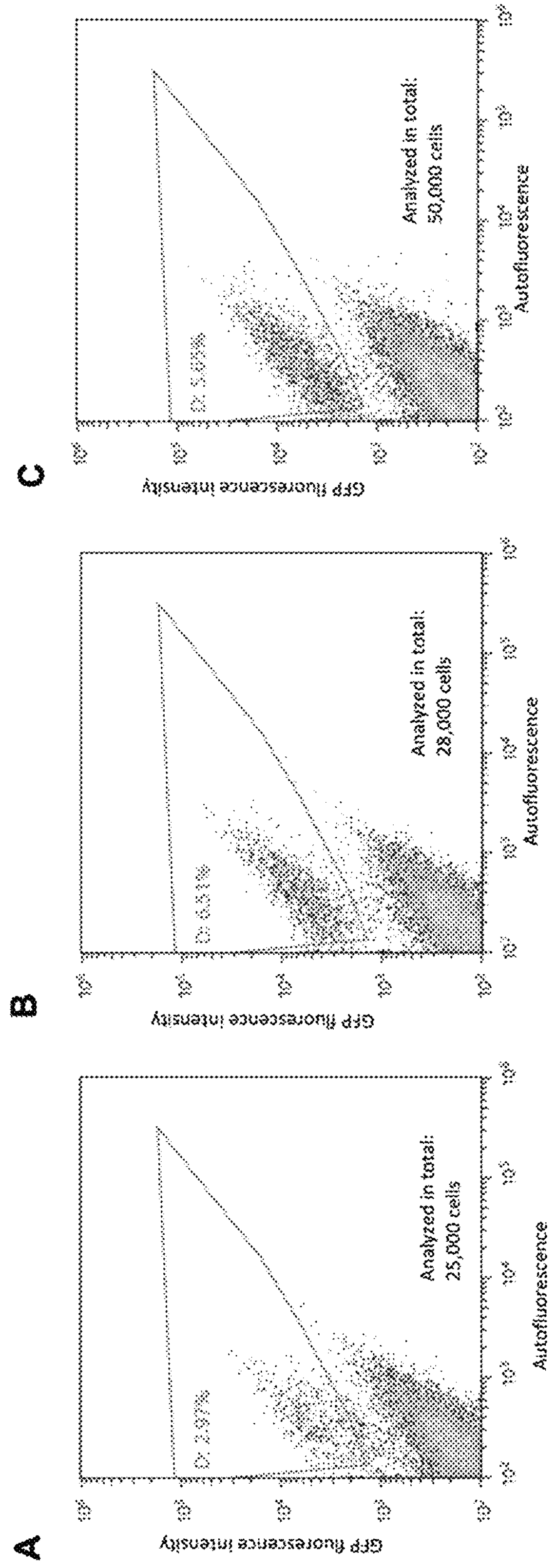

FIG. 12 Tagging rates when targeting the CANX gene and A) the conventional GFP donor plasmid, B) the same amount of minicircle DNA and C) one third the amount of minicircle DNA.

Figure 13:
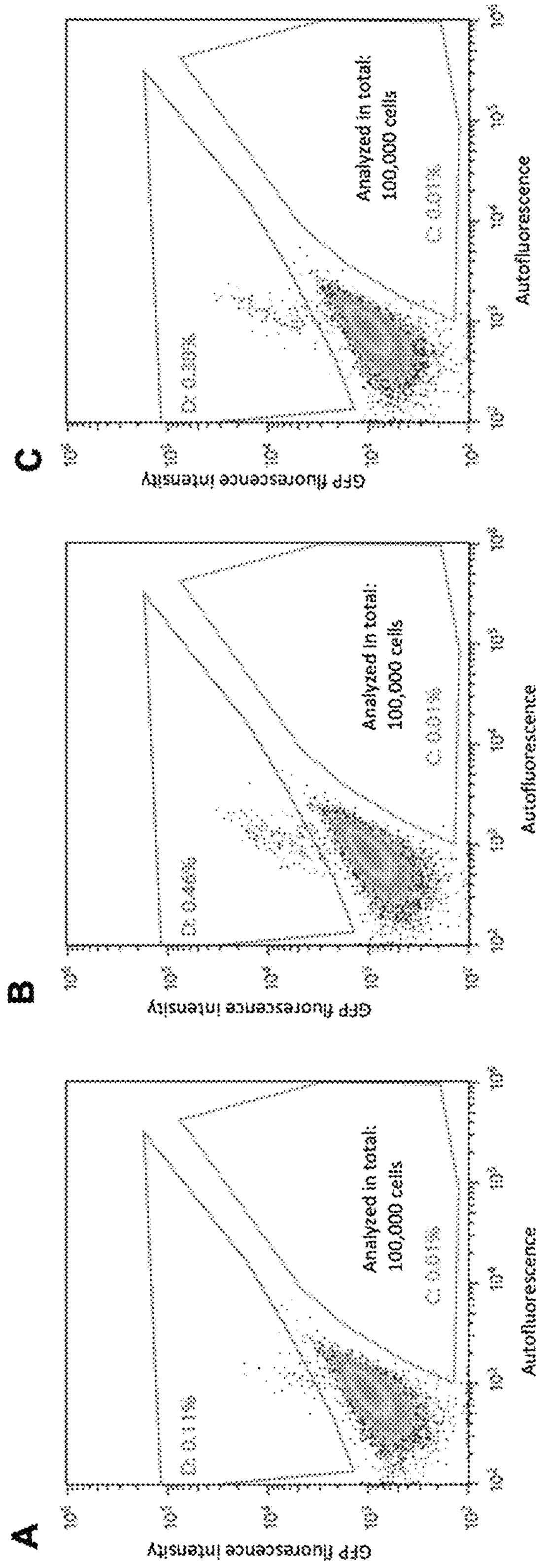

FIG. 13 Tagging rates when targeting the CANX gene and A) the conventional GFP donor plasmid, B) the same amount of minicircle DNA and C) one third the amount of minicircle DNA in cell populations that were not enriched for transfected cells.

Example 1: Employed Methods

Generation of an Intron-Targeting sgRNA Library

To design an intron-targeting sgRNA library for metabolic enzymes and epigenetic modifiers a list of 2,889 genes was generated by combining a published list of all classic metabolic enzymes (see, Corcoran (2017) Am J Physiol Renal Physiol 312, F533-F542), most genes in a human CRISPR metabolic gene knockout library (see; Birsoyv (2015) Cell 162, 540-51) as well as genes annotated with the GO terms "Histone modification", "DNA methylation" or "DNA demethylation". Then, the Ensembl BioMart data mining tool was used to obtain chromosomal coordinates of introns of the primary transcripts of those genes and only those introns were selected where integration of the donor plasmid does not lead to frameshift mutations after splicing, since the donor plasmid starts with a full codon and is not compatible to all exon-exon junctions. Using Ensembl BioMart this filtering was done by only selecting introns that are preceded by an exon with the attribute "End phase=0". The GuideScan (Perez, 2017, Nat Biotechnol 35, 347-349) was then used to obtain the top 20 guides for each selected intronic region based on the GuideScan cutting efficiency score. Those 20 guides were then ranked based on a combined on- and off-target score using the scores provided by GuideScan. For genes that have only one intron that can be targeted, up to three sgRNAs per intron were selected, for genes with two or three introns that can be targeted, up to 2 sgRNAs per intron were selected and for genes that have more than three introns that can be targeted, the top ranked sgRNA of each intron was selected. Using that strategy, 14,049 sgRNAs targeting 11,614 introns of 2,387 genes were selected. In addition, 75 non-targeting sgRNAs from the human Brunello CRISPR KO library (Doench, 2016, Nat Biotechnol 34, 184-191) were added to the library. For cloning of the library into the CROPseq-Guide-Puro vector16 (Addgene #86708) using Gibson Assembly, adapter sequences were added to the sgRNA sequences and 74 nucleotide oligos were ordered as an oligo pool (Twist Biosciences). Additional adapters were added to the pooled oligos by PCR (8 cycles, NEB Q5) to generate fragments with a size of 140 nucleotides that were purified (QIAGEN MinElute PCR Purification) before being used for Gibson Assembly. The vector was digested with BsmBI (NEB), size-selected using agarose gel electrophoresis and gel purified (QIAGEN QIAquick Gel Extraction Kit) followed by an additional column purification (QIAGEN QIAquick PCR Purification Kit). 4 Gibson Assembly reactions (10 μl NEBuilder HiFi DNA Assembly, 60 ng vector, 10 ng insert) were prepared and incubated at 50° C. for 45 minutes. Reactions were pooled and purified (QIAGEN MinElute PCR Purification) before being used for transformation in Lucigen Endura electrocompetent bacteria (four reactions, 25 μl each). Bacteria were plated on four 245×245×25 mm Bioassay dishes and dilution plates (1:10,000) and incubated at 32° C. for 16 h. Cells were scraped off the plates and plasmid DNA was extracted using multiple QIAGEN Plasmid Plus Midi kits. Library coverage was 211× and was estimated based on the number of colonies on the dilution plates.

Cloning

The GFP-donor plasmid with the coding sequence of EGFP flanked by generic sgRNA targeting sites, splice acceptor and splice donor sites and 20 amino acid linkers was assembled from 4 fragments using Gibson Assembly to generate a donor plasmid that is similar in design to a previously published donor plasmid that can be used for intron tagging; see Feldman (2019) Cell 179, 787-799 e17. The DNA fragment with a 25 nucleotide overlap to the pUC19 vector and 32 nucleotide overlap to the N-terminus of EGFP was generated from overlapping oligos (Sigma) and comprises a generic sgRNA targeting site that is not present in the human genome (He, 2016,. Nucleic Acids Res 44, e85) followed by a splice acceptor site (Guzzardo, 2017, Sci Rep 7, 16770) and a flexible 20 amino acid glycine-serine linker. This fragment is followed by a fragment with the coding sequence of EGFP without a start or stop codon that was generated by PCR. The third fragment has a 27 nucleotide overlap to the C-terminus of EGFP and a 25 nucleotide overlap to the pUC19 vector and was generated from overlapping oligos (Sigma) and comprises a flexible 20 amino acid glycine-serine linker followed by a splice donor site (Guzzardo, 2017, loc, cit) the generic sgRNA targeting site. The pUC19 vector was linearized by PCR for Gibson Assembly (NEBuilder HiFi DNA Assembly) with the other three fragments.

The pX330 plasmid expressing Cas9 and the generic sgRNA targeting the donor plasmid was generated by digesting pU6-(Bbsl)_CBh-Cas9-T2A-mCherry (Addgene #64324; see also Chu, 2015, Nat Biotechnol 33, 543-8) with Bbsl followed by ligation with an annealed oligo duplex as described before; see, Ran (2013), Nat Protoc 8, 2281-2308. mCherry was replaced with a Blasticidin resistance (BSD) using Gibson Assembly.

Pooled Protein Tagging

For the generation of lentiviral particles, HEK293T cells were transiently transfected with the intron-targeting library and packaging plasmids psPAX2, pMD2.G using PEI transfection. After 12 h the media was replaced with IMDM supplemented with 10% FBS and P/S. Viral supernatant was collected 48 h after transfection and stored at −80° C. HAP1 cells were transduced with virus and selected with puromycin for three days. Multiplicity of infection (MOI) was 0.2 and transduction was done at a coverage of 500×. After puromycin selection, cells were grown for one day in media without puromycin before being seeded for transfection (8 million cells per 15 cm dish, 48 million cells in total). One day after seeding, each dish was co-transfected with 20 μg pX330 expressing Cas9-BSD and the generic sgRNA and 10 μg EGFP donor plasmid with 90 μl Turbofection in 2.5 ml OptiMEM as described by the manufacturer. Transfection efficiency was approximately 10% as determined by a transfection done in parallel with pX330 Cas9-mCherry and the EGFP donor plasmid using the same ratio. The next day, cells were subjected to a transient selection using Blasticidin (10 μg/ml) for 24 h. After selection, cells were maintained in full media without Blasticidin and sorted five days after transfection by flow cytometry using a Sony Cell Sorter SH800ZD. 0.03% cells were GFP-positive and in total 24,300 of those GFP-positive cells were sorted and the cell population was expanded for 7 days before DNA was isolated to determine sgRNA abundance in the cell population.

NGS Sequencing

In order to generate an NGS library, genomic DNA from one million cells of the GFP positive cell population was isolated and the sgRNA region was amplified by PCR (two reactions using 500 ng genomic DNA, NEB Q5 high-fidelity Polymerase). Illumina adapter ligation and sequencing were done by a commercial sequencing service. To determine sgRNA abundance, sgRNA sequences were extracted from NGS reads using Cutadapt and sgRNA read counts were determined using the MAGeCK count function to match the extracted reads to the sgRNA library. Of the 14,049 sgRNA in the library we considered 1,777 as highly enriched as these sgRNAs accounted for 90% of the obtained sequencing reads while the majority of sgRNAs was not detectable anymore. The remaining 10% of sequencing reads comprise an additional 1,622 sgRNAs, which we do not consider as enriched, as each of them is only supported by a few sequencing reads that might be the result of cells being transduced with two sgRNAs or the result of off-target integration and expression of the GFP-tag. Our library also includes 75 nontargeting sgRNAs making up 0.53% of the sgRNAs in our library. As expected, they are depleted in the pool of GFP-positive, making up 0.15% of the sequencing reads with only 3 non-targeting sgRNAs among the 1,777 sgRNAs we consider enriched.

Isolation, Imaging and Sequencing of Clonal Cell Lines

To obtain clonal cell lines, cells were seeded at a concentration of 0.7 cells per well in 96-well cell culture plates. After 9 days of clonal expansion, 768 colonies were harvested using trypsin and cell suspensions were transferred in equal amounts to eight 96-well imaging plates (Perkin Elmer CellCarrier Ultra) and eight corresponding 96-well cell culture plates. After 24 h, cells on the imaging plates were imaged on a Perkin Elmer Opera Phenix High Content Screening System (5 fields of view per well, 63× water-immersion objective, confocal mode, excitation: 488 nm, emission: nm, 700 ms). Images were processed using Cell Profiler. To identify the intron-targeting sgRNAs expressed in imaged cells, multiplexed amplicon sequencing of the sgRNA regions was performed in the corresponding clones on the eight 96-well cell culture plates. Cells were lysed and cell lysates were used for PCR to amplify the sgRNA region in each clone using barcoded primers flanking the sgRNA region (36 different 5-mers added to the 5'end of the forward primer and 24 different 5-mers added to the 5'end of the reverse primer, 768 of all possible 864 combinations were used). PCR reactions were pooled and column purified before being send for sequencing by a commercial sequencing service. NGS reads were demultiplexed using Cutadapt (see Martin, M. EMBnet. journal, [S.I.], v. 17, n. 1, p. pp. 10-12, may 2011) and sgRNA read counts for each individual well were obtained using MAGeCK (see, Li (2014) Genome Biol 15, 554 (2014). For further analysis clones were excluded, for which either no cells in any of the 5 fields of view that were imaged were observed, no sequencing reads for the corresponding well were observed or for which polyclonal cell populations as determined by imaging or detection of multiple sgRNAs per well were observed. Using that strategy, images of 335 clones were obtained for which the expressed intron-targeting sgRNA corresponding to the tagged protein could be identified.

Comparison of Subcellular Localization to the Human Protein Atlas

Comparison of subcellular protein localizations of GFP-tagged protein in 335 clones to the localization patterns as annotated on The Human Protein Atlas was done as described previously for the comparison of N- or C-terminally GFP-tagged proteins to IF-based annotations on the Human Protein Atlas, see Stadler (2013) Nat Methods 10, 315-23. Briefly, the overlap was defined as 'identical' if one or multiple main and additional localizations were the same in the intron-tagged clone compared to The Human Protein Atlas, 'similar' if one localization is the same in the clone compared to The Human Protein Atlas with additional localization(s) observed either in the clone or on The Human Protein atlas or 'dissimilar' if there were no common subcellular localization patterns. Extended localization annotations such as nucleoplasm, nuclear speckles or nucleoli that were considered as "nuclear" were not taken into account.

Live Cell Imaging

Live cell imaging was performed on a PerkinElmer Opera Phenix microscope with excitation laser 488 nm, and emission filter 500-550 nm, 700 ms.

In Situ Sequencing

Identification of the expressed sgRNAs by in situ sequencing was performed by following and modifying published protocols, see, e.g., Feldman (2019) loc. cit; Ke (2013) Nat Methods 10, 857-60; and Larsson (2010) Nat Methods 7, 395-7.

After live-cell imaging after treatment with MTX or dBET6, cells were fixed with 4% paraformaldehyde for 30 minutes, washed with PBS, permeabilized with 70% ethanol for 30 minutes and washed with PBS-T (PBS+0.05% Tween-20) twice. Reverse transcription mix (1× RevertAid RT buffer, 250 μM dNTPs, 0.2 mg/mL BSA, 1 μM RT primer, 0.8 U/mL Ribolock RNase inhibitor, and 4.8 U/mL RevertAid H minus reverse transcriptase) was added to the sample and incubated for 16 hours at 37° C. Following reverse transcription, cells were washed 5 times with PBS-T and post-fixed with 3% paraformaldehyde and 0.1% glutaraldehyde for 30 minutes at room temperature and washed 5 times with PBS-T. Cells were incubated in a padlock probe and extension-ligation reaction mix (1× Ampligase buffer, 0.4 U/mL RNase H, 0.2 mg/mL BSA, 100 nM padlock probe, 0.02 U/mL KlenTaq polymerase, 0.5 U/mL Ampligase and 50 nM dNTPs) for 5 minutes at 37° C. and 90 minutes at 45° C., and then washed 2 times with PBS-T. Circularized padlocks were amplified with rolling circle amplification mix (1× Phi29 buffer, 250 μM dNTPs, 0.2 mg/mL BSA, 5% glycerol, and 1 U/mL Phi29 DNA polymerase) at 30° C. for 4 hours. Rolling circle amplicons were prepared for sequencing by hybridizing a mix containing sequencing primer oSBS_CROP-seq (1 μM primer in 2×SSC+10% formamide) for 30 minutes at room temperature. Barcodes were read out using sequencing-by-synthesis reagents from the Illumina NextSeq 500/550 kit v2 (Illumina 15057934). First, samples were washed with incorporation buffer (NextSeq 500/550 buffer cartridge, position 35) and incubated for 4 minutes in incorporation mix (NextSeq 500/550 reagent cartridge, position 31) at 60° C. Samples were then washed with incorporation buffer (4 washes, 60° C. for 4 minutes at the last wash) and placed in scan mix (NextSeq 500/550 reagent cartridge, position 30) for imaging. Imaging was performed on a PerkinElmer Opera Phenix microscope with excitation laser: 561 nm, emission filter: 570-630, 500 ms; excitation laser: 640 nm, emission filter: 650-760 nm, 500 ms using a 63× water immersion objective, confocal mode. Based were detected as follows: Base T: signal in 561 channel; Base C: signal in 640 channel, Base A: (weaker) signal in both channels, Base G: no signal. Following each imaging cycle, samples were washed with the cleavage mix (NextSeq 500/550 reagent cartridge, position 29) once followed by incubation with cleavage mix for 4 minutes at 60° C. to remove dye terminators. Samples were washed 5 times with incorporation buffer before starting the next cycle.

```
Primer Sequences employed:
NGS Sequencing
CROP-seq sgRNA amplicon fwd
                                        (SEQ ID NO: 1)
ATCTTGTGGAAAGGACGAAACACC

CROP-seq sgRNA amplicon rev
                                        (SEQ ID NO: 2)
tgtctcaagatctagttacgcca

in situ sequencing
oRT_CROPseq
                                        (SEQ ID NO: 3)
G+AC+TA+GC+CT+TA+TT+TTAACTTGCTAT
(Feldman et al.)

oPD_CROPseq
                                        (SEQ ID NO: 4)
/5Phos/gttttagagctagaaatagcaagCTCCTGTT

CGACACCTACCCACCTCATCCCACTCTTCAaaaggacg

aaacaccg
(Feldman et al.)

oSBS_CROPseq
                                        (SEQ ID NO: 5)
CACCTCATCCCACTCTTCAaaaggacgaaacaccg
Feldman et al.

multiplexed amplicon sequencing barcodes
FWD1_1
                                        (SEQ ID NO: 6)
GAGAAATCTTGTGGAAAGGACGAAACAC

FWD1_2
                                        (SEQ ID NO: 7)
CAAGAATCTTGTGGAAAGGACGAAACAC

FWD1_3
                                        (SEQ ID NO: 8)
GAACAATCTTGTGGAAAGGACGAAACAC

FWD1_4
                                        (SEQ ID NO: 9)
CCATAATCTTGTGGAAAGGACGAAACAC

FWD1_5
                                       (SEQ ID NO: 10)
GTTAGATCTTGTGGAAAGGACGAAACAC

FWD1_6
                                       (SEQ ID NO: 11)
ACTCGATCTTGTGGAAAGGACGAAACAC

FWD1_7
                                       (SEQ ID NO: 12)
TGTTGATCTTGTGGAAAGGACGAAACAC

FWD1_8
                                       (SEQ ID NO: 13)
AGGTCATCTTGTGGAAAGGACGAAACAC

FWD1_9
                                       (SEQ ID NO: 14)
AGGAAATCTTGTGGAAAGGACGAAACAC

FWD1_10
                                       (SEQ ID NO: 15)
ACAGAATCTTGTGGAAAGGACGAAACAC
```

-continued

```
FWD1_11
                                       (SEQ ID NO: 16)
AGACAATCTTGTGGAAAGGACGAAACAC

FWD1_12
                                       (SEQ ID NO: 17)
TGGTAATCTTGTGGAAAGGACGAAACAC

FWD2_1
                                       (SEQ ID NO: 18)
CTAGGATCTTGTGGAAAGGACGAAACAC

FWD2_2
                                       (SEQ ID NO: 19)
CGATGATCTTGTGGAAAGGACGAAACAC

FWD2_3
                                       (SEQ ID NO: 20)
TTCGCATCTTGTGGAAAGGACGAAACAC

FWD2_4
                                       (SEQ ID NO: 21)
GGTTCATCTTGTGGAAAGGACGAAACAC

FWD2_5
                                       (SEQ ID NO: 22)
CCGAAATCTTGTGGAAAGGACGAAACAC

FWD2_6
                                       (SEQ ID NO: 23)
TCGGAATCTTGTGGAAAGGACGAAACAC

FWD2_7
                                       (SEQ ID NO: 24)
AAGCAATCTTGTGGAAAGGACGAAACAC

FWD2_8
                                       (SEQ ID NO: 25)
TCCTAATCTTGTGGAAAGGACGAAACAC

FWD2_9
                                       (SEQ ID NO: 26)
AATGGATCTTGTGGAAAGGACGAAACAC

FWD2_10
                                       (SEQ ID NO: 27)
GCATGATCTTGTGGAAAGGACGAAACAC

FWD2 11
                                       (SEQ ID NO: 28)
TATGCATCTTGTGGAAAGGACGAAACAC

FWD2_12
                                       (SEQ ID NO: 29)
CCTGTATCTTGTGGAAAGGACGAAACAC

FWD3_1
                                       (SEQ ID NO: 30)
GTGGAATCTTGTGGAAAGGACGAAACAC

FWD3_2
                                       (SEQ ID NO: 31)
CTGCAATCTTGTGGAAAGGACGAAACAC

FWD3_3
                                       (SEQ ID NO: 32)
ACCAAATCTTGTGGAAAGGACGAAACAC

FWD3_4
                                       (SEQ ID NO: 33)
TGCGAATCTTGTGGAAAGGACGAAACAC

FWD3_5
                                       (SEQ ID NO: 34)
TGTCAATCTTGTGGAAAGGACGAAACAC

FWD3_6
                                       (SEQ ID NO: 35)
TAGAGATCTTGTGGAAAGGACGAAACAC
```

-continued

FWD3_7 (SEQ ID NO: 36)

TACCGATCTTGTGGAAAGGACGAAACAC

FWD3_8 (SEQ ID NO: 37)

TTGTGATCTTGTGGAAAGGACGAAACAC

FWD3_9 (SEQ ID NO: 38)

ACACCATCTTGTGGAAAGGACGAAACAC

FWD3_10 (SEQ ID NO: 39)

ACCTTATCTTGTGGAAAGGACGAAACAC

FWD3_11 (SEQ ID NO: 40)

CTCTAATCTTGTGGAAAGGACGAAACAC

FWD3_12 (SEQ ID NO: 41)

TCACGATCTTGTGGAAAGGACGAAACAC

REV1_A (SEQ ID NO: 42)

GGCAATGTCTCAAGATCTAGTTACGCCA

REV1_B (SEQ ID NO: 43)

AACGATGTCTCAAGATCTAGTTACGCCA

REV1_C (SEQ ID NO: 44)

GTCCATGTCTCAAGATCTAGTTACGCCA

REV1_D (SEQ ID NO: 45)

TGAAGTGTCTCAAGATCTAGTTACGCCA

REV1_E (SEQ ID NO: 46)

GTACGTGTCTCAAGATCTAGTTACGCCA

REV1_F (SEQ ID NO: 47)

ACGTGTGTCTCAAGATCTAGTTACGCCA

REV1_G (SEQ ID NO: 48)

CAACCTGTCTCAAGATCTAGTTACGCCA

REV1_H (SEQ ID NO: 49)

CACTTTGTCTCAAGATCTAGTTACGCCA

REV2_A (SEQ ID NO: 50)

CGTAATGTCTCAAGATCTAGTTACGCCA

REV2_B (SEQ ID NO: 51)

GGTGATGTCTCAAGATCTAGTTACGCCA

REV2_C (SEQ ID NO: 52)

CCTCATGTCTCAAGATCTAGTTACGCCA

REV2_D (SEQ ID NO: 53)

ATGAGTGTCTCAAGATCTAGTTACGCCA

REV2_E (SEQ ID NO: 54)

ATCCGTGTCTCAAGATCTAGTTACGCCA

REV2_F (SEQ ID NO: 55)

GACTGTGTCTCAAGATCTAGTTACGCCA

-continued

REV2_G (SEQ ID NO: 56)

TCTCCTGTCTCAAGATCTAGTTACGCCA

REV2_H (SEQ ID NO: 57)

GCTAATGTCTCAAGATCTAGTTACGCCA

REV3_A (SEQ ID NO: 58)

CTTGATGTCTCAAGATCTAGTTACGCCA

REV3_B (SEQ ID NO: 59)

GGATATGTCTCAAGATCTAGTTACGCCA

REV3_C (SEQ ID NO: 60)

AGTAGTGTCTCAAGATCTAGTTACGCCA

REV3 D (SEQ ID NO: 61)

GATCGTGTCTCAAGATCTAGTTACGCCA

REV3_E (SEQ ID NO: 62)

AGCTGTGTCTCAAGATCTAGTTACGCCA

REV3_F (SEQ ID NO: 63)

CTTCCTGTCTCAAGATCTAGTTACGCCA

REV3_G (SEQ ID NO: 64)

ATTGCTGTCTCAAGATCTAGTTACGCCA

REV3_H (SEQ ID NO: 65)

GTGCTTGTCTCAAGATCTAGTTACGCCA

GFP generic donor plasmid (relevant part) (SEQ ID NO: 66)

atgttctttcctgcgttatcccctggagatcgagtgccgca tcacCGGCTATTGGTCTTACTGACATCCACTTTGCCTTTC TCTCCACAGggggcggtggctcgggcggtggtgggtccgg tggcggcggatctggcggtggtggatccgtgagcaagggc gaggagctgttcaccggggtggtgcccatcctggtcgagc tggacggcgacgtaaacggccacaagttcagcgtgtccgg cgagggcgagggcgatgccacctacggcaagctgaccctg aagttcatctgcaccaccggcaagctgcccgtgccctggc ccaccctcgtgaccaccctgacctacggcgtgcagtgctt cagccgctaccccgaccacatgaagcagcacgacttcttc aagtccgccatgcccgaaggctacgtccaggagcgcacca tcttcttcaaggacgacggcaactacaagacccgcgccga ggtgaagttcgagggcgacaccctggtgaaccgcatcgag ctgaagggcatcgacttcaaggaggacggcaacatcctgg ggcacaagctggagtacaactacaacagccacaacgtcta tatcatggccgacaagcagaagaacggcatcaaggtgaac ttcaagatccgccacaacatcgaggacggcagcgtgcagc tcgccgaccactaccagcagaacacccccatcggcgacgg ccccgtgctgctgcccgacaaccactacctgagcacccag tccgccctgagcaaagaccccaacgagaagcgcgatcaca -continued

```
tggtcctgctggagttcgtgaccgccgccgggatcactct

cggcatggacgagctgtacaagggcggcggtggatccggt

ggcggcggatctggcggtggaggttcgggtggcggtgggt

cgggcaagGTAAGTATCAATTAGAAGACGAATTCCCGgtg

atgcggcactcgatctcGAATTCttacagacaagctgtga

ccgtctccgggagctgcatgtgtcagaggttttcaccgtc

atcaccgaaacgcgcgagacgaaagggcctcgtgatacgc

ctatttttataggttaatgtcatgataataatgg
```

Example 2: Generation of a Cell Pool Comprising Protein Tagging and Being Employed for Cellular Imaging and In Situ Sequencing-Novel Means and Methods for Real Time Drug Testing and/or Screening The present invention relates to the provision of a large cell pool that comprises individual intro-tagged proteins.

As illustrative, non limiting example of the means and methods of the present invention, a pooled GFP (green fluorescent protein)-intron-tagging of metabolic enzymes is provided herein. As provided herein, a CRISPR/Cas9 mediated intron tagging approach is employed to generate a large pool of cells herein with more than 900 tagged proteins, wherein each cell comprises one tagged protein, i.e. a "one protein per cell" approach is provided. The inventive means and methods of the present invention offer the following advantages, namely that (i) by designing the sgRNA target genes can be chosen as desired (ii) by designing the sgRNA different introns for the same genes can be chosen, allowing to avoid tagging within functionally important domains and (iii) that very homogenous distributions of cells can be generated with roughly equal numbers of clones for each targeted protein.

A second key aspect of the inventive method is the application of in situ sequencing. Following exposure of the inventive cell pool to molecules to be screened (for example. drugs and/or pharmacologically relevant molecules), some cells respond with changes in protein localization or in protein abundance (measured by fluorescence microscopy of the GFP tag fused to the protein). The application of a CROP-seq vector as provided and illustrated herein for the intron-targeting sgRNA library allows for in situ sequencing in order to identify the tagged intron. In order to render this compatible with the provided illustrative GFP tagged cell pool, the in situ sequencing protocol was adopted to a two color system Accordingly, a CRISPR-Cas9 based intron tagging is employed herein to generate cell pools expressing hundreds of labeled/tagged-fusion proteins at endogenous levels, to monitor drug effects on protein levels and/or to localization by time-lapse microscopy. Furthermore, within the means and methods of the present invention is the identification of targeted introns by in situ sequencing. Accordingly, the means and methods of the present invention provide for a pooled protein tagging approach allowing for the localization and even (expression) levels of hundreds of proteins in individual cells in real time; see also illustrative FIG. 2*a*

In context of the present invention, 2,889 genes were selected to be targeted comprising all classic metabolic enzymes and epigenetic modifiers; see Corcoran (2017). Am J Physiol Renal Physiol 312, F533-F542; Birsoy (2015), Cell 162, 540-51. For the 2,387 genes from this set that harbor targetable introns in the selected reading frame, a library comprising 14,049 sgRNAs targeting 11,614 introns (FIG. 2*b*) was designed. To generate a pool of GFP-tagged cells, HAP1 cells were transduced with that sgRNA library followed by co-transfection with a GFP donor plasmid and a plasmid expressing Cas9 and the donor-targeting sgRNA. It was enriched for transfected cells using blasticidin for 24 h and sorted GFP-positive cells 6 days after transfection (FIG. 2*c*). NGS-based sgRNA amplicon sequencing of the pool of GFP-positive cells identified 1,777 sgRNAs targeting 1,650 introns of 953 genes as highly enriched in the GFP-positive cell pool (FIG. 2*d*). Compared to genes for which intron targeting sgRNAs did not result in isolation of GFP positive cells, successfully targeted genes have higher average expression in HAP1 cells (FIG. 2*e*). Clonal cell lines were then isolated from the pool by single cell dilution and clonal expansion, in which GFP localization was imaged (FIG. 2*f*) and sgRNAs were identified indicating the tagged proteins by an NGS-based multiplex sgRNA amplicon sequencing strategy. After removing cell lines in which more than one sgRNA was present, 362 clonal lines were obtained. The main localization of GFP-tagged proteins in the majority of our cell lines was either cytoplasmic, nuclear or mitochondrial, with some proteins showing a typical ER localization pattern. These localization corresponded to the antibody-based annotations in the Human Protein Atlas (Thul, 2017, Science 356) in 72% of the clones (FIG. 2*f*), and for 40 GFP-tagged proteins in the clonal cell lines no previous localization data is available.

It was reasoned that the highly diverse pool of cells expressing GFP-tagged proteins can be used to identify compounds that change protein levels or localization of any of the tagged proteins. Therefore, the cell pool was treated with the BRD4-targeting PROTAC dBET6 (Winter (2017). Mol Cell 67, 5-18 e19) and high-content live cell imaging was used to track protein dynamics of GFP-tagged proteins over 9 hours in approximately 7,000 cells in a single well on a 384-well plate (FIG. 6*a*). A drastic loss of GFP signal was observed in selected clones already 1 h after compound treatment. These clones had a nuclear GFP localization pattern with few selected foci, compatible with the known phase separation behavior of BRD4 (FIG. 6*b*); see also Sabari (2018) Science 361. The application of the CROP-seq vector16 that expresses the sgRNA sequence in a polyadenylated mRNA transcript enables the cell-specific identification of the targeted intron by situ sequencing (see also Feldman, D. et al. Cell 179, 787-799 el 7 (2019), Ke, R. et al. Nat Methods 10, 857-60 (2013), Larsson, C. et al. Nat Methods 7, 395-7 (2010). 17-19). To map targeted introns, the cell pool was fixed and a modified in situ sequencing protocol was developed to identify the sgRNA sequence integrated into individual cells in the pool. Based on the library diversity, eight cycles of nucleotide incorporation and imaging are sufficient to unambiguously assign sgRNA sequences (FIG. 6*c*). Application of this protocol to the cell pool confirmed that in clones with drastic loss of signal GFP was indeed targeted to BRD4 (FIG. 6*d*). Analysis of the entire cell pool revealed several other effects of the compound, including the loss of subnuclear localization patterns of MEAF1 and FUBP3, gain of nuclear foci of AKAP8 and SFPQ, and loss of nuclear intensity for UNG (FIG. 6*e*), none of which are identifiable by global proteomics profiling; see also Winter (2017), loc. cit..

It was then tested whether the cell pool also reveals complex cellular responses to compounds that act by conventional mechanisms. Therefore the cell pool was treated with methotrexate (MTX), an antimetabolite impairing DNA and RNA synthesis and causing DNA damage by inhibiting tetrahydrofolate metabolism. Changes to the localizations of several proteins were observed in the cell pool (FIG. 10*a*), which could be further validated by applying MTX to the arrayed individual clones (FIG. 10*b*). Importantly, many of the findings are consistent with the known effects of the drug. For example, 24 h MTX treatment caused increased nuclear localization of GFP-tagged ACLY, a metabolic enzyme that has been shown to translocate to the nucleus in response to DNA damage; Sivanand (2017) Mol Cell 67, 252-265 e6. In cell lines expressing either GFP-tagged RPA1 or RPA2, which are part of a heterotrimeric DNA single-strand binding complex, the formation of nuclear foci was observed in response to treatment, presumably by the recruitment of the proteins to sites of DNA damage; see Raderschall (1999), Proc Natl Acad Sci USA 96, 1921-6. In addition to these predicted effects, a gain of nuclear signal for TPI1, NUDT21 and the transcription factor DR1, the disappearance of nuclear DNMT1 foci, and decreases of RUVBL1 and PADI1 protein was also noted. Importantly, some of the observations are supported by multiple clonal cell lines expressing the same GFP-tagged protein tagged at different intronic sites or by multiple proteins that are part of the same complex, increasing the confidence in the observed drug effects on different proteins.

The generation of targeted GFP tagged cell pools enables, inter alia, the identification of cellular drug responses by time lapse microscopy. Future applications of the present invention and corresponding uses, including deep learning and image recognition as well as direct in situ sequencing, will further accelerate the assignment of the targeted clones directly from screening well. Importantly, the low cost and fast timescales of imaging-based approaches enable applications both in large scale screening and in the rapid optimization of doses and response kinetics in a cellular system. This approach is especially useful for the discovery and development of PROTACs and molecular glue degraders, for which activity can easily be determined by the disappearance of the tagged protein, however we document herein also that the means and methods of the present invention can be employed to verify and/or confirm known drug actions and/or to discover new effects of known drugs. Importantly, intron tagging can easily be applied for other sets of genes beyond metabolic enzymes and potentially in a genome-wide manner to study protein dynamics at scale not only in response to drug treatment or other physiological perturbations.

Example 3—Minicircle Plasmids

For protein tagging with an intron tagging strategy, a generic sgRNA is excising a fluorescent tag flanked by splice acceptor and donor sites from a generic donor plasmid. This excision was done by cutting the donor plasmid twice, resulting in the fragment containing the coding sequence of the tag flanked by splice acceptor and a splice donor (FIG. 11A). However, another fragment containing the plasmid backbone is generated and this fragment is equally likely getting integrated at target sites as specified by an intron targeting sgRNA. If the plasmid backbone gets integrated, these target sites are not available anymore for integration of GFP containing plasmid, thereby lowering the editing efficiency (FIG. 11B). Furthermore, it was observed that in some cases the donor plasmid is cut only once, leading to integration of the entire linearized plasmid containing not only the coding sequence of the protein tag, but also the plasmid backbone containing sequences for plasmid amplification on bacteria (origin of replication, resistance gene etc., FIG. 11C). While cells with those integrations would still be GFP positive, it was observed that integration of the plasmid backbone can change levels of or correct localization of GFP-fusions. Here it is shown that using a minicircle that contains only the coding sequence of the protein tag flanked by splice acceptor and donor sites and has only one generic sgRNA target site to linearize the minicircle, significantly improves the intron tagging strategy by addressing both disadvantages of the current strategy (FIG. 11D).

To compare the conventional donor plasmid to a minicircle, it was attempted to tag CANX at intron 14 by using either a GFP donor plasmid containing two generic sgRNA sites or a GFP minicircle containing only one generic sgRNA sites and no plasmid backbone. A tagging rate of 3.0% was achieved when using the GFP donor plasmid as determined by analyzing transfected cells by flow cytometry (FIG. 12A). When using the GFP minicircle, the tagging rate increased approximately two-fold to 6.5% (FIG. 12B). To rule out that the observed increase is only resulting from a higher number of transfected fragments (GFP minicircle is 1 kb in length compared to the 3 kb GFP donor plasmid, which is why 200 ng of GFP minicircle contains three times as many molecules as 200 ng of GFP donor plasmid) a third sample was transfected with ⅓ the amount of donor plasmid (67 ng) and again an improved tagging rate of 5.7% was observed (FIG. 12C). Therefore, it was concluded that the improved tagging rate is not simply the result of a higher number of fragments that are present in the cell, but is due to the design of the minicircle, making integration of any plasmid backbone fragment impossible. Additionally, when using the minicircle it is not possible to integrate the GFP containing fragment together with the plasmid backbone as observed when the conventional donor plasmid is only cut once and linearized plasmid gets integrated. These integrations can result in lower expression levels of tagged genes and indeed less GFP-positive cells with intensity levels only slightly above the autofluorescence of cells were observed (note the very distinct GFP-positive population in the two minicircle samples compared to the population in the GFP donor plasmid sample).

In a second independent experiment, similar improvements when using the minicircle were observed (4-fold increase in GFP-positive cells when using the same amount of GFP minicircle DNA as GFP donor plasmid and 3-fold when using ⅓ the amount of minicircle DNA) but in this experiment the overall tagging rates were lower due to lower transfection efficiency (less than 10% of cells that were analyzed were transfected, FIG. 13A-C).

Minicircle DNA was produced with a commercial minicircle production kit (SBI MC-Easy™ Minicircle DNA Production Kit). First, a parental production plasmid was generated by cloning a DNA fragment starting with the generic sgRNA target site followed by a splice acceptor, a 20 amino acid linker sequence, the coding sequence of EGFP, another 20 amino acid linker sequence and a splice donor site into the pMC.BESPX-MCS1 production plasmid. The DNA fragment was generated by PCR using the GFP donor plasmid as a template, pMC.BESPX-MCS1 was digested with EcoRV and the fragment was integrated at the restriction site via Gibson Assembly. The *E. coli* producer strain ZYCY10P3S2T was transformed with the ligation reaction and clonal bacterial colonies were selected for isolation and sequencing of parental plasmid. A colony containing the correct parental plasmid was used for minicircle production as described by the manufacturer. In brief, bacteria were grown overnight in the provided growth media and induction media was added the next day to induce att recombination and parental plasmid backbone degradation. Minicircle DNA was isolated from bacterial pellets using multiple Qiagen Plasmid Plus Midi kits and the produced minicircle was analyzed by restriction enzyme digest and gel electrophoresis.

For intron tagging experiments, A549 cells were cells seeded in a 12-well plate and were co-transfected with 400 ng of the CROPseq plasmid expressing the intron-targeting sgRNA targeting intron 14 of the CANX gene, 400 ng of the pX330 plasmid expressing Cas9-mCherry and the donor-targeting sgRNA, together with 200 ng of the GFP donor plasmid or 200 ng GFP minicircle using Lipofectamine 3000 as described by the manufacturer. In samples with ⅓ of the amount of GFP minicircle, cells were cotransfected with 467 ng of the CROPseq plasmid with the intron-targeting sgRNA targeting intron 14 of the CANX gene, 467 ng of the pX330 plasmid expressing Cas9-mCherry and the donor-targeting sgRNA, and 67 ng GFP minicircle. To enrich for transfected cells, mCherry-positive cells were sorted 48 h after transfection and expanded for one week before GFP-positive cells were sorted. In an independent experiment a px330 plasmid expressing Cas9-BSD instead of Cas9-mCherry was used, cells were not enriched for transfected cells and GFP-positive cells were sorted 48 h after transfection.

Annotation and sequence of the parental GFP minicircle production plasmid:

| | |
|---|---|
| 1-738 | 32 consecutive ISce1 site |
| 782-816 | attB site |
| 852-871 | generic sgRNA target site |
| 872-874 | PAM site |
| 875-916 | splice acceptor |
| 917-976 | 20-amino-acid-linker |
| 977-1690 | EGFP |
| 1691-1753 | 21-amino-acid-linker |
| 1754-1776 | splice donor |
| 1812-1850 | attP site |
| 1937-2731 | Kanamycin resistance |
| 3034-5071 | EcoE1 origin |

Only the sequence between the attB and attP site circularizes and remains in the final GFP minicircle.

Only the part between the attB and attP sites was designed. The parental producer plasmid backbone is part of the commercial SBI MC-Easy™ Minicircle DNA Production Kit.

(SCQ ID NC: 67)

ACATTACCCTGTTATCCCTAGATACATTACCCTGTTATCCC

AGATGACATACCCTGTTATCCCTAGATGACATTACCCTGT

TATCCCAGATGACATTACCCTGTTATCCCTAGATACATTA

CCCTGTTATCCCAGATGACATACCCTGTTATCCCTAGATG

ACATTACCCTGTTATCCCAGATGACATTACCCTGTTATCC

CTAGATACATTACCCTGTTATCCCAGATGACATACCCTGT

TATCCCTAGATGACATTACCCTGTTATCCCAGATGACATT

ACCCTGTTATCCCTAGATACATTACCCTGTTATCCCAGAT

-continued

GACATACCCTGTTATCCCTAGATGACATTACCCTGTTATC

CCAGATGACATTACCCTGTTATCCCTAGATACATTACCCT

GTTATCCCAGATGACATACCCTGTTATCCCTAGATGACAT

TACCCTGTTATCCCAGATGACATTACCCTGTTATCCCTAG

ATACATTACCCTGTTATCCCAGATGACATACCCTGTTATC

CCTAGATGACATTACCCTGTTATCCCAGATGACATTACCC

TGTTATCCCTAGATACATTACCCTGTTATCCCAGATGACA

TACCCTGTTATCCCTAGATGACATTACCCTGTTATCCCAG

ATGACATTACCCTGTTATCCCTAGATACATTACCCTGTTA

TCCCAGATGACATACCCTGTTATCCCTAGATGACATTACC

CTGTTATCCCAGATAAACTCAATGATGATGATGATGATGG

TCGAGACTCAGCGGCCGCGGTGCCAGGGCGTGCCCTTGGG

CTCCCCGGGCGCGACTAGTGAATTCAGATCTGATCCTGCG

TTATCCCCTGGAGATCGAGTGCCGCATCACCGGCTATTGG

TCTTACTGACATCCACTTTGCCTTTCTCTCCACAGGGTGG

CGGTGGCTCGGGCGGTGGTGGGTCCGGTGGCGGCGGATCT

GGCGGTGGTGGATCCGTGAGCAAGGGCGAGGAGCTGTTCA

CCGGGGGGTGCCCATCCTGGTCGAGCTGGACGGCGACGTA

AACGGCCACAAGTTCAGCGTGTCCGGCGAGGGCGAGGGCG

ATGCCACCTACGGCAAGCTGACCCTGAAGTTCATCTGCAC

CACCGGCAAGCTGCCCGTGCCCTGGCCCACCCTCGTGACC

ACCCTGACCTACGGCGTGCAGTGCTTCAGCCGCTACCCCG

ACCACATGAAGCAGCACGACTTCTTCAAGTCCGCCATGCC

CGAAGGCTACGTCCAGGAGCGCACCATCTTCTTCAAGGAC

GACGGCAACTACAAGACCCGCGCCGAGGTGAAGTTCGAGG

GCGACACCCTGGTGAACCGCATCGAGCTGAAGGGCATCGA

CTTCAAGGAGGACGGCAACATCCTGGGGCACAAGCTGGAG

TACAACTACAACAGCCACAACGTCTATATCATGGCCGACA

AGCAGAAGAACGGCATCAAGGTGAACTTCAAGATCCGCCA

CAACATCGAGGACGGCAGCGTGCAGCTCGCCGACCACTAC

CAGCAGAACACCCCCATCGGCGACGGCCCCGTGCTGCTGC

CCGACAACCACTACCTGAGCACCCAGTCCGCCCTGAGCAA

AGACCCCAACGAGAAGCGCGATCACATGGTCCTGCTGGAG

TTCGTGACCGCCGCCGGGATCACTCTCGGCATGGACGAGC

TGTACAAGGGCGGCGGTGGATCCGGTGGCGGCGGATCTGG

CGGTGGAGGTTCGGGTGGCGGTGGGTCGGGCAAGGTAAGT

ATCAATTAGAAGACGAATTCCATCTCTAGAGTCGACCCAT

GGGGGCCCGCCCCAACTGGGGTAACCTTTGAGTTCTCTCA

GTTGGGGGTAATCAGCATCATGATGTGGTACCACATCATG

ATGCTGATTATAAGAATGCGGCCGCCACACTCTAGTGGAT

CTCGAGTTAATAATTCAGAAGAACTCGTCAAGAAGGCGAT

AGAAGGCGATGCGCTGCGAATCGGGAGCGGCGATACCGTA
AAGCACGAGGAAGCGGTCAGCCCATTCGCCGCCAAGCTCT
TCAGCAATATCACGGGTAGCCAACGCTATGTCCTGATAGC
GGTCCGCCACACCCAGCCGGCCACAGTCGATGAATCCAGA
AAAGCGGCCATTTTCCACCATGATATTCGGCAAGCAGGCA
TCGCCATGGGTCACGACGAGATCCTCGCCGTCGGGCATGC
TCGCCTTGAGCCTGGCGAACAGTTCGGCTGGCGCGAGCCC
CTGATGCTCTTCGTCCAGATCATCCTGATCGACAAGACCG
GCTTCCATCCGAGTACGTGCTCGCTCGATGCGATGTTTCG
CTTGGTGGTCGAATGGGCAGGTAGCCGGATCAAGCGTATG
CAGCCGCCGCATTGCATCAGCCATGATGGATACTTTCTCG
GCAGGAGCAAGGTGAGATGACAGGAGATCCTGCCCCGGCA
CTTCGCCCAATAGCAGCCAGTCCCTTCCCGCTTCAGTGAC
AACGTCGAGCACAGCTGCGCAAGGAACGCCCGTCGTGGCC
AGCCACGATAGCCGCGCTGCCTCGTCTTGCAGTTCATTCA
GGGCACCGGACAGGTCGGTCTTGACAAAAAGAACCGGGCG
CCCCTGCGCTGACAGCCGGAACACGGCGGCATCAGAGCAG
CCGATTGTCTGTTGTGCCCAGTCATAGCCGAATAGCCTCT
CCACCCAAGCGGCCGGAGAACCTGCGTGCAATCCATCTTG
TTCAATCATGCGAAACGATCCTCATCCTGTCTCTTGATCA
GAGCTTGATCCCCTGCGCCATCAGATCCTTGGCGGCGAGA
AAGCCATCCAGTTTACTTTGCAGGGCTTCCCAACCTTACC
AGAGGGCGCCCCAGCTGGCAATTCCGGTTCGCTTGCTGTC
CATAAAACCGCCCAGTCTAGCTATCGCCATGTAAGCCCAC
TGCAAGCTACCTGCTTTCTCTTTGCGCTTGCGTTTTCCCT
TGTCCAGATAGCCCAGTAGCTGACATTCATCCGGGGTCAG
CACCGTTTCTGCGGACTGGCTTTCTACGTGCTCGAGGGGG
GCCAAACGGTCTCCAGCTTGGCTGTTTTGGCGGATGAGAG
AAGATTTTCAGCCTGATACAGATTAAATCAGAACGCAGAA
GCGGTCTGATAAAACAGAATTTGCCTGGCGGCAGTAGCGC
GGTGGTCCCACCTGACCCCATGCCGAACTCAGAAGTGAAA
CGCCGTAGCGCCGATGGTAGTGTGGGGTCTCCCCATGCGA
GAGTAGGGAACTGCCAGGCATCAAATAAAACGAAAGGCTC
AGTCGAAAGACTGGGCCTTTCGTTTTATCTGTTGTTTGTC
GGTGAACGCTCTCCTGAGTAGGACAAATCCGCCGGGAGCG
GATTTGAACGTTGCGAAGCAACGGCCCGGAGGGTGGCGGG
CAGGACGCCCGCCATAAACTGCCAGGCATCAAATTAAGCA
GAAGGCCATCCTGACGGATGGCCTTTTTGCGTTTCTACAA
ACTCTTTTGTTTATTTTTCTAAATACATTCAAATATGTAT
CCGCTCATGACCAAAATCCCTTAACGTGAGTTTTCGTTCC

ACTGAGCGTCAGACCCCGTAGAAAAGATCAAAGGATCTTC
TTGAGATCCTTTTTTTCTGCGCGTAATCTGCTGCTTGCAA
ACAAAAAAACCACCGCTACCAGCGGTGGTTTGTTTGCCGG
ATCAAGAGCTACCAACTCTTTTTCCGAAGGTAACTGGCTT
CAGCAGAGCGCAGATACCAAATACTGTCCTTCTAGTGTAG
CCGTAGTTAGGCCACCACTTCAAGAACTCTGTAGCACCGC
CTACATACCTCGCTCTGCTAATCCTGTTACCAGTGGCTGC
TGCCAGTGGCGATAAGTCGTGTCTTACCGGGTTGGACTCA
AGACGATAGTTACCGGATAAGGCGCAGCGGTCGGGCTGAA
CGGGGGGTTCGTGCACACAGCCCAGCTTGGAGCGAACGAC
CTACACCGAACTGAGATACCTACAGCGTGAGCTATGAGAA
AGCGCCACGCTTCCCGAAGGGAGAAAGGCGGACAGGTATC
CGGTAAGCGGCAGGGTCGGAACAGGAGAGCGCACGAGGGA
GCTTCCAGGGGGAAACGCCTGGTATCTTTATAGTCCTGTC
GGGTTTCGCCACCTCTGACTTGAGCGTCGATTTTTGTGAT
GCTCGTCAGGGGGGGGAGCCTATGGAAAAACGCCAGCAAC
GCGGCCTTTTTACGGTTCCTGGCCTTTTGCTGGCCTTTTG
CTCACATGTTCTTTCCTGCGTTATCCCCTGATTCTGTGGA
TAACCGTATTACCGCCTTTGAGTGAGCTGATACCGCTCGC
CGCAGCCGAACGACCGAGCGCAGCGAGTCAGTGAGCGAGG
AAGCGGAAGAGCGCCTGATGCGGTATTTTCTCCTTACGCA
TCTGTGCGGTATTTCACACCGCATATGGTGCACTCTCAGT
ACAATCTGCTCTGATGCCGCATAGTTAAGCCAGTATACAC
TCCGCTATCGCTACGTGACTGGGTCATGGCTGCGCCCCGA
CACCCGCCAACACCCGCTGACGCGCCCTGACGGGCTTGTC
TGCTCCCGGCATCCGCTTACAGACAAGCTGTGACCGTCTC
CGGGAGCTGCATGTGTCAGAGGTTTTCACCGTCATCACCG
AAACGCGCGAGGCAGCAGATCAATTCGCGCGCGAAGGCGA
AGCGGCATGCATAATGTGCCTGTCAAATGGACGAAGCAGG
GATTCTGCAAACCCTATGCTACTCCGTCAAGCCGTCAATT
GTCTGATTCGTTACCAATTATGACAACTTGACGGCTACAT
CATTCACTTTTTCTTCACAACCGGCACGGAACTCGCTCGG
GCTGGCCCCGGTGCATTTTTTAAATACCCGCGAGAAATAG
AGTTGATCGTCAAAACCAACATTGCGACCGACGGTGGCGA
TAGGCATCCGGGTGGTGCTCAAAAGCAGCTTCGCCTGGCT
GATACGTTGGTCCTCGCGCCAGCTTAAGACGCTAATCCCT
AACTGCTGGCGGAAAAGATGTGACAGACGCGACGGCGACA
AGCAAACATGCTGTGCGACGCTGGCGAT

The invention claimed is:

1. A method for monitoring the effect of an environmental factor on the proteome of a cell, the method comprising the steps of:

(a) selecting introns to be targeted in the genome of a cell;

(b) identifying guide RNA (gRNA) sequences suitable for inserting a tag sequence in the selected introns in the genome of the cell;

(c) cloning the identified gRNA sequences and the tag sequence into vectors;

(d) contacting a population of the cell with said vectors of (c) to integrate the tag sequence of (b) into the selected introns;

(e) exposing the cell population to the environmental factor; and (f) monitoring the effect of the environmental factor on the proteome based on the detection of the tag sequence prior to exposure of the cell population to the environmental factor and subsequent to exposure of the cell population to the environmental factor.

2. The method of claim 1, further comprising a sequencing step subsequent to step (d) or (f).

3. The method of claim 2, wherein the gRNA insert of (a) cell(s) of the population is sequenced in the genome of said cell(s) or in the transcriptome of said cell(s).

4. The method of claim 1, wherein the transduction vector is a sequencing vector.

5. The method of claim 1, wherein the introns to be targeted are comprised in genomic sequences of metabolic enzymes, chromatin proteins, kinases, genes coding for proteins in the ubiquitin/proteasome pathways, transcription factors, ion channels, transporters, or receptors; and/or wherein at least one intron per protein coding gene in the genome is targeted; and/or wherein the introns to be targeted are selected based on the reading frame of the upstream exonic sequence, wherein the sequence to be inserted is in-frame with the exonic sequence.

6. The method of claim 1, wherein the gRNA sequences suitable for inserting the tag sequence in the selected introns in the genome of the cell are identified according to cas9 cutting efficiency or Cpf1 cutting efficiency or Cas12b cutting efficiency, and/or wherein the gRNA sequences suitable for inserting the tag sequence in the selected introns in the genome of the cell are identified according to their occurrence in the genome of the cell.

7. The method of claim 1, wherein the gRNA is a single gRNA (sgRNA).

8. The method of claim 1, wherein the environmental factor is radiation, a chemical compound, a biological compound, temperature, nutrient depletion, or ion concentration(s); and/or wherein the effect on the proteome comprises a change in protein expression, protein localization, surface expression, protein-protein interaction, protein stability, or protein mobility; and/or wherein the cell is a HAP1 cell, K562 cell, HeLa cell, KBM7 cell, BT474 cell, MG-63 cell, SKNAS cell, A427 cell, A375 cell, A498 cell, RCH-ACV cell, HEK293T cell, A673 cell, SK-N-MC cell, A549 cell, SKMES1 cell, NCIH727 cell, THP1 cell, NB4 cell, MOLM13 cell, KASUMI-1 cell, HEL cell, NB-4 cell, HL-60 cell, RS4-11 cell, MOLT7 cell, aTC1 cell, bTC3 cell, or Min6 cell; and/or wherein the tag sequence encodes a fluorescence tag or a protein tag suitable for detection by covalent or non-covalent binding to a detection reagent enabling detection by microscopy.

9. The method of claim 1, further comprising a step of separating tagged cells from non-tagged cells.

10. The method of claim 1, wherein in step (c) the identified gRNA sequences are cloned into a transduction vector.

11. The method of claim 10, wherein in step (c) the tag sequence is cloned into a donor plasmid or minicircle DNA.

12. The method of claim 1, wherein in step (c) the tag sequence is cloned into a donor plasmid or minicircle DNA.

13. The method of claim 4, wherein the sequencing vector is a Crop-Seq vector.

14. The method of claim 6, wherein the occurrence is 1.

15. The method of claim 1, wherein the cell is an adherent, non-migratory cell line.

16. The method of claim 8, wherein the fluorescence tag is GFP, EGFP, YFP, or RFP.

17. The method of claim 8, wherein the protein tag suitable for detection by covalent binding to a detection reagent is a Halo tag, Clip tag, or Snap tag.

18. The method of claim 8, wherein the protein tag suitable for detection by non-covalent binding to a detection reagent is a Strep-tag, HA tag, or dTag.

19. The method of claim 8, wherein the detection by microscopy comprises the detection of fluorescence or luminescence.

20. The method of claim 9, wherein the tagged and non-tagged cells are separated using FACS.

* * * * *